United States Patent [19]

Petersen

[11] Patent Number: 4,675,045

[45] Date of Patent: Jun. 23, 1987

[54] HERBICIDAL SULFONAMIDES

[75] Inventor: Wallace C. Petersen, Hockessin, Del.

[73] Assignee: E. I. Du Pont de Nemours and Company, Wilmington, Del.

[21] Appl. No.: 856,781

[22] Filed: May 2, 1986

Related U.S. Application Data

[63] Continuation-in-part of Ser. No. 740,029, May 31, 1985, abandoned.

[51] Int. Cl.$^4$ .............. C07D 239/69; C07D 401/12; C07D 409/12; A01N 43/54

[52] U.S. Cl. ........................... 71/90; 71/92; 544/321; 544/331; 544/332; 544/122; 544/123; 544/82; 544/211; 544/212; 544/219; 544/278; 540/601

[58] Field of Search ............ 71/90, 92; 544/321, 544/331, 332, 122, 123, 82; 540/601

[56] References Cited

U.S. PATENT DOCUMENTS 4,486,589  12/1984  Farnham ........................ 544/211
4,545,808  10/1985  Levitt .............................. 544/321

Primary Examiner—John M. Ford

[57] ABSTRACT

Thiocarbonylsulfonylureas, useful as herbicides and plant growth regulants, herbicidal compositions employing these compounds and methods of applying them to soil or directly to plants have been discovered.

58 Claims, No Drawings

HERBICIDAL SULFONAMIDES

Related Application

This application is a continuation-in-part of U.S. Ser. No. 740,029, filed May 31, 1985, now abandoned.

BACKGROUND OF THE INVENTION

This invention relates to sulfonylureas useful as herbicides and plant growth regulants. More particularly, it relates to o-thiocarbonylsulfonylureas having useful herbicidal and plant growth regulant activity.

U.S. Pat. No. 4,394,506 teaches herbicidal carboxylic ester sulfonylureas of the formula

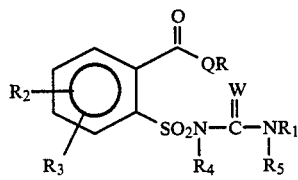

where, in part,

Q is O, S or $NR_6$;

R is $C_1$-$C_{12}$ alkyl, $C_3$-$C_{10}$ alkenyl, $C_3$-$C_{10}$ alkynyl, $C_2$-$C_6$ alkyl substituted with 1-4 substituents selected from 0-3 atoms of F, Cl or Br, 0-2 methoxy groups and 0-1 cyano group; $CH_2Cl$; $CH(R_7')CO_2CH_3$ or $CH(R_7')CO_2C_2H_5$ where $R_7'$ is H or $CH_3$; $C_3$-$C_6$ alkenyl substituted with 1-3 atoms of F, Cl or Br; etc.

$R_2$ is H, Cl, Br, F, $C_1$-$C_3$ alkyl, $NO_2$, etc.

$R_3$ is H, Cl, Br, F or $CH_3$;

$R_4$ is H or $CH_3$;

$R_5$ is H, $CH_3$ or $OCH_3$;

$R_6$ is H, $C_1$-$C_6$ alkyl, allyl, $CH_2CN$ or $CH_2CH_2CN$; and

R and $R_6$ can be taken together to form $(CH_2)_4$, $(CH_2)_5$, $(CH_2)_6$, $CH_2CH_2OCH_2CH_2$ or $CH_2CH_2N(CH_3)CH_2CH_2$.

U.S. Pat. No. 4,348,219 discloses herbicidal phenylacetic ester sulfonylureas of the formula

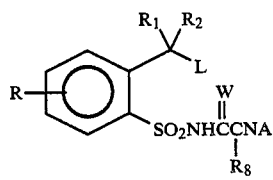

wherein

L is $CO_2R_{10}$, $CONR_3R_4$ or CN;

R is H, F, Cl, Br, $NO_2$, $CF_3$, $C_1$-$C_3$ alkyl or $C_1$-$C_3$ alkoxy;

$R_1$ is H or $C_1$-$C_4$ alkyl;

$R_2$ is H or $CH_3$;

$R_8$ is H, $CH_3$ or $OCH_3$; and

W is O or S.

U.S. Pat. No. 4,420,325 covers herbicidal benzylsulfonylureas of the formula

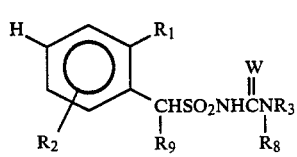

wherein $R_1$ is inter alia, F, Cl, Br, $CF_3$, $C_1$-$C_3$ alkoxy, $C_1$-$C_3$ alkyl;

$R_2$ is H, Cl, Br, F, $CF_3$ or $OCH_3$;

$R_9$ is H or $C_1$-$C_3$ alkyl;

W is O or S;

$R_8$ is H or $CH_3$; etc.

U.S Pat. No. 4,481,029 teaches herbicidal sulfonylureas of Formulae I, II and III:

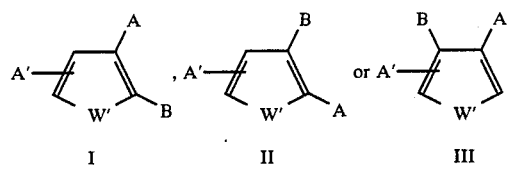

wherein

W' is O or S;

A' is H, Cl, Br, $C_1$-$C_4$ alkyl, $OCH_3$, $NO_2$ or $CF_3$;

A is $C(O)QR^I$ or $C(T)R^{II}$;

Q is O, S or $NR_6$;

$R^I$ is inter alia, $C_1$-$C_6$ alkyl or $C_3$-$C_6$ alkenyl;

B is

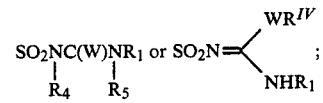

etc.

European Patent Application No. 95,925 (published Dec. 7, 1983) discloses, in part, herbicidal sulfonylureas of the formula

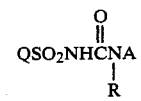

wherein

Q is, inter alia,

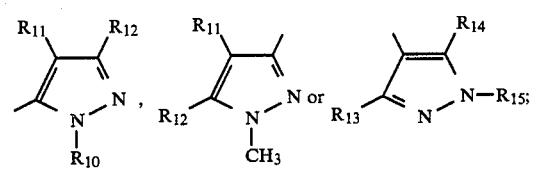

R is H or $CH_3$;

$R_{10}$ is H, $C_1$-$C_4$ alkyl, $C_3$-$C_4$ alkenyl, etc.;

$R_{11}$ is H, $C_1$-$C_3$ alkyl, F, Cl, Br, $NO_2$, etc.

$R_{12}$ is H or $CH_3$;

$R_{13}$ and $R_{14}$ are independently H, $C_1$-$C_3$ alkyl, $OR_{16}$, F, Cl, Br, etc.;

$R_{15}$ is H or $CH_3$; etc.

U.S. Pat. Nos. 4,544,401 and 4,435,206 disclose herbicidal pyridinesulfonylureas.

The presence of undesired vegetation causes substantial damage to useful crops, especially agricultural products that satisfy man's basic food needs, such as soybeans, barley, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials, useful for killing, or inhibiting (controlling) the growth of undesired vegetation is available; such materials are commonly referred to as herbicides. The need exists, however, for still more effective herbicides that destroy or retard weeds without causing signficant damage to useful crops.

SUMMARY OF THE INVENTION

This invention relates to novel compounds of Formula 1, agriculturally suitable compositions containing them, and their method-of-use as general preemergence and/or postemergence herbicides, or plant growth regulants.

$$JSO_2NHCNA \quad I$$
$$\underset{R}{|} \overset{W}{\|}$$

wherein
J is

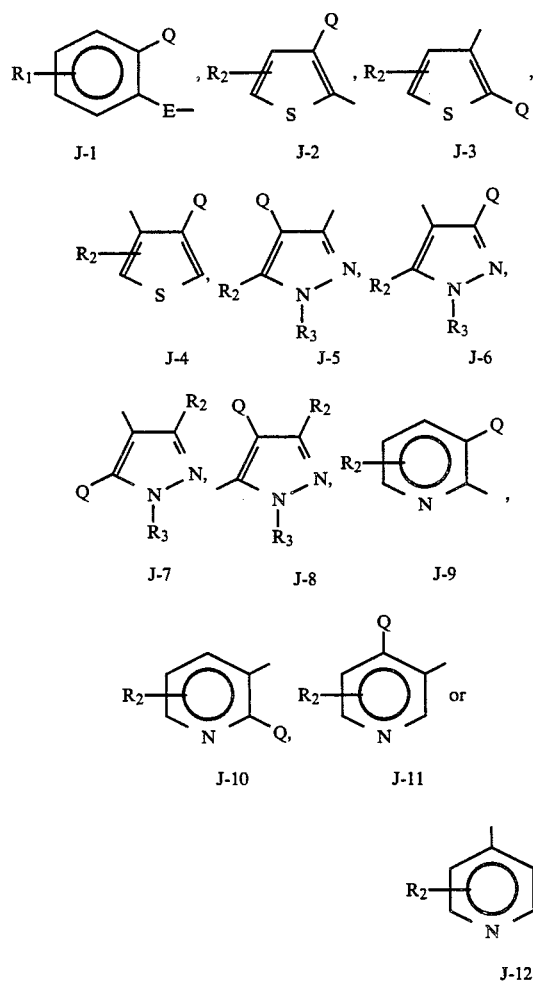

W is O or S;
R is H or $CH_3$;
E is a single bond or $-CH_2-$;
Q is $Q_1$, $Q_2$ or $Q_3$;
$Q_1$ is

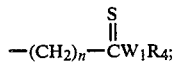

$Q_2$ is

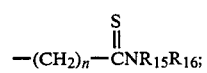

$Q_3$ is

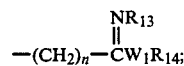

n is 0 or 1; $W_1$ is O or S;

R is H, $C_1-C_4$ alkyl, $C_1-C_3$ haloalkyl, Cl, Br, F, $NO_2$, $C_1-C_3$ alkoxy, $SO_2NR_aR_b$, $C_1-C_3$ alkylthio, $C_1-C_3$ alkylsulfinyl, $C_1-C_3$ alkylsulfonyl, CN, $CO_2R_c$, $C_1-C_3$ haloalkoxy, $C_1-C_3$ haloalkylthio, $CH_2OCH_3$, $CH_2SCH_3$, $CH_2CN$, $NH_2$, $NHCH_3$ or $N(CH_3)_2$;

$R_2$ is H, Cl, Br, $C_1-C_4$ alkyl, $C_1-C_3$ alkoxy or $C_1-C_3$ alkylthio;

$R_3$ is H, $C_1-C_4$ alkyl, $C_3-C_4$ alkenyl or phenyl;

$R_a$ is H, $C_1-C_4$ alkyl, $C_2-C_3$ cyanoalkyl or $C_1-C_3$ alkoxy;

$R_b$ is H, $C_1-C_4$ alkyl or $C_3-C_4$ alkenyl; or $R_a$ and $R_b$ may be taken together as $(CH_2)_3$, $(CH_2)_4$, $(CH_2)_5$ or $CH_2CH_2OCH_2CH_2$;

$R_c$ is $C_1-C_4$ alkyl, $C_3-C_4$ alkenyl, $C_3-C_4$ alkynyl, $C_2-C_4$ haloalkyl, $C_2-C_3$ cyanoalkyl, $C_5-C_6$ cycloalkyl, $C_4-C_7$ cycloalkylalkyl or $C_2-C_4$ alkoxyalkyl;

$R_4$ is $C_1-C_{12}$ alkyl, $C_3-C_{10}$ alkenyl, $C_3-C_{10}$ alkynyl, $C_2-C_6$ alkyl substituted with 1-4 substitutents selected from
(a) 0-3 atoms of F, Cl or Br,
(b) 0-2 $OCH_3$ groups.
(c) 0-1 $C_2-C_3$ alkoxy, phenoxy, chloroethoxy or trichloroethoxy groups,
(d) 0-2 substituents selected from OH, $OC(O)R_5$, $OC(O)OR_5$, $OC(O)NR_5R_6$, $OP(O)(OR_7)_2$, $OSO_2R_5$, $OSO_2NR_5R_6$, $OSi(R_8)_2R_7$ or $S(O)_mR_5$, or
(e) 0-1 cyano group,
$CH_2CN$, $CH_2OR_9$, $CH(R_{10})CO_2CH_3$, $CH(R_{10})CO_2C_2H_5$, $C_3-C_6$ haloalkenyl, $C_3-C_6$ haloalkynyl, $C_5-C_8$ cycloalkyl, $C_5-C_8$ cycloalkenyl, $C_4-C_{10}$ cycloalkylalkyl, $C_4-C_8$ cycloalkylalkyl substituted with 1-2 $CH_3$ groups, $C_5-C_6$ cycloalkyl substituted with
(a) $OCH_3$,
(b) $C_2-C_4$ alkyl,
(c) F, Cl or Br, or
(d) 1-4 $CH_3$ groups.

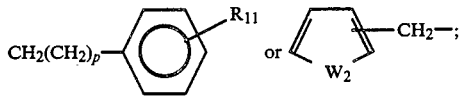

$R_5$ is $C_1-C_4$ alkyl substituted with 0-3 atoms of F, Cl or Br, 0-2 $OCH_3$ groups or 0-1 CN, $C_3-C_4$ alkenyl substituted with 0-3 atoms of F, Cl or Br, $C_3-C_4$ alkynyl or

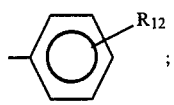

$R_6$ is H or $C_1$–$C_2$ alkyl;
$R_7$ is $C_1$–$C_4$ alkyl or phenyl;
$R_8$ is $C_1$–$C_2$ alkyl;
m is 0, 1 or 2;
p is 0 or 1;
$w_2$ is O or S;
$R_9$ is $C_1$–$C_3$ alkyl, chloroethyl, trichloroethyl, phenyl, $CH_2CH_2OCH_3$, $CH_2CH_2OC_2H_5$ or

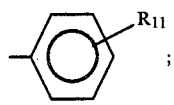

$R_{10}$ is H or $CH_3$;
$R_{11}$ is H, $C_1$–$C_3$ alkyl, Cl, Br, $OCH_3$ or $OC_2H_5$;
$R_{12}$ is H, F, Cl, Br, $CH_3$, $OCH_3$, $SCH_3$, $SO_2CH_3$, $NO_2$ or $CF_3$;
$R_{13}$ is $C_1$–$C_4$ alkyl;
$R_{14}$ is $C_1$–$C_4$ alkyl;
$R_{15}$ is H, $C_1$–$C_6$ alkyl, $C_2$–$C_3$ alkyl substituted with $C_1$–$C_3$ alkoxy or phenoxy, $C_3$–$C_6$ alkenyl, $C_3$–$C_6$ alkynyl, $C_3$–$C_6$ cycloalkyl, $C_5$–$C_6$ cycloalkenyl, $C_4$–$C_7$ cycloalkylalkyl, $C_5$–$C_6$ cycloalkyl substituted with $CH_3$ or $OCH_3$, $CH_2CN$, $CH_2CH_2CN$, $OCH_3$, $OC_2H_5N(CH_3)_2$

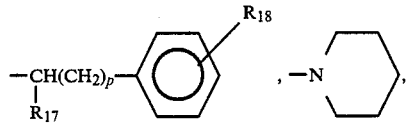

$R_{16}$ is H $C_1$–$C_6$ alkyl, $CH_2CH=CH_2$, $CH_2CN$ or $CH_2CH_2CN$; or
$R_{15}$ and $R_{16}$ may be taken together to form $(CH_2)_3$, $(CH_2)_4$, $(CH_2)_5$, $(CH_2)_6$, $CH_2CH=CHCH_2$, $CH_2CH_2OCH_2CH_2$ or $CH_2CH_2N(CH_3)CH_2CH_2$;
$R_{17}$ is H or $CH_3$;
$R_{18}$ is H, $C_1$–$C_3$ alkyl, Cl, Br, $OCH_3$ or $OC_2H_5$;
$R_{19}$ is H, $C_1$–$C_4$ alkyl, $OCH_3$, F, Br, Cl, $CF_3$, CN, $NO_2$, $SO_2CH_3$, $SCH_3$ or $N(CH_3)_2$;
A is

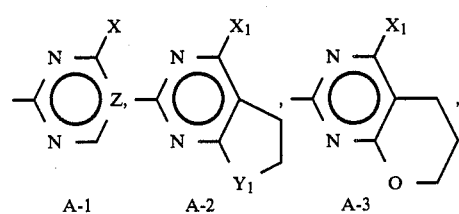

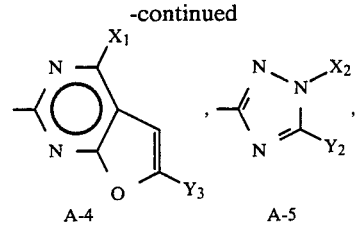

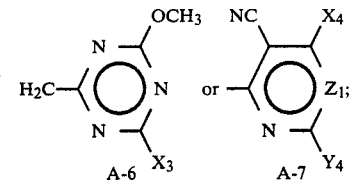

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen $C_2$–$C_5$ alkoxyalkoxy, amino, $C_1$–$C_3$ alkylamino or di($C_1$–$C_3$)alkylamino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di ($C_1$–$C_3$)alkylamino, $C_3$–$C_4$ alkenyloxy, $C_3$–$C_4$ alkynyloxy, $C_2$–$C_5$ alkylsulfinylalkyl, $C_1$–$C_4$ haloalkyl, $C_2$–$C_5$ alkylsulfonylalkyl, $C_3$–$C_5$ cycloalkyl, $C_2$–$C_4$ alkynyl, $C_2$–$C_5$ alkylthioalkyl,

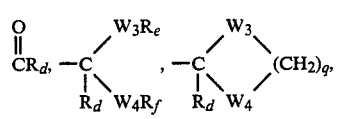

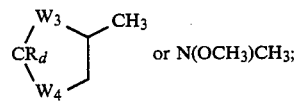

$W_3$ and $W_4$ are independently O or S;
q is 2 or 3;
$R_d$ is H or $CH_3$;
$R_e$ is $C_1$–$C_2$ alkyl;
$R_f$ is $C_1$–$C_2$ alkyl;
Z is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $OCF_2H$, $SCF_2H$, $CH_3$ or $CH_2CH_3$;
$X_3$ is $CH_3$ or $OCH_3$;
$Y_3$ is H or $CH_3$;
$Z_1$ is CH or N;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts;
provided that
(a) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

(b) when X is Cl, Br, F or I, then Z is CH and Y is $OCH_3$, $OC_2H_5$, $NH_2$, $NHCH_3$, $N(CH_3)_2$ or $OCF_2H$;

(c) when X or Y is $C_1$ haloalkoxy, then Z is CH;

(d) the total number of carbon atoms of $R_4$ is less than or equal to 13;

(e) the combined total number of carbon atoms of $R_{15}$ and $R_{16}$ is less than or equal to 10;

(f) when $R_{15}$ is $CH_2CN$ or $CH_2CH_2CN$, then $R_{16}$ is $CH_2CN$ or $CH_2CH_2CN$;

(g) when $R_{15}$ is $OCH_3$ or $OC_2H_5$ then $R_{16}$ is H or $CH_3$;

(h) when $R_4$ is disubstituted with substituents selected from OH, $OC(O)R_5$, $OC(O)OR_5$, $OC(O)NR_5R_6$, $OP(O)(OR_7)_2$, $OSO_2R_5$, $OSO_2NR_5R_6$, $OSi(R_8)_2R_7$ or $S(O)_mR_5$, then the two substituents are identical and are not on the same carbon atom, and the carbon atom bonded to $W_1$ does not bear any of the above substituents and must be substituted by at least one hydrogen atom;

(i) when E is $CH_2$, then n is 0;

(j) when the total number of carbon atoms of X and Y is greater than four, then the number of carbons of $R_1$ is less than or equal to two, the number of carbons of $R_2$ is less than or equal to two, and the number of carbons of Q is less than or equal to four; and (k) $x_4$ and $Y_4$ are not simultaneously Cl.

In the above definitions, the term "alkyl", used either alone or in compound words such as "alkylthio" or "haloalkyl", denotes straight chain or branched x alkyl , e.g. methyl, ethyl n-propyl, isopropyl or the different butyl, pentyl, hexyl, heptyl, octyl, nonyl, decyl, undecyl or dodecyl isomers.

Alkoxy denotes methoxy, ethoxy, n-propyloxy, isopropyloxy and the different butyl isomers.

Alkenyl denotes straight chain or branched alkenes, e.g. vinyl, 1-propenyl, 2-propenyl, 3-propenyl and the different butenyl, pentenyl, hexenyl, heptenyl, octenyl, nonenyl or decenyl isomers.

Alkynyl denotes straight chain or branched alkynes, ethynyl 1-propynyl, 2-propynyl and the different butynyl, pentynyl, hexynyl, heptynyl, octynyl, nonynyl and decynyl isomers.

Alkylsulfonyl denotes methylsulfonyl, ethylsulfonyl and the different propylsulfonyl and butylsulfonyl isomers.

Alkylthio, alkylsulfinyl, alkylamino, alkylsulfamoyl, etc, are defined in an analogous manner.

Cycloalkyl denotes, e.g. cyclopropyl, cyclobutyl, cyclopentyl or cyclohexyl. Cycloalkenyl means cyclopentenyl or cyclohexenyl.

The term "halogen", either alone or in compound words such as "haloalkyl", denotes fluorine, chlorine, bromine or iodine.

The total number of carbon atoms in a substituent group is indicated by the $C_i$-$C_j$ prefix where i and j are numbers from 1 to 12. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$. The term $C_4$-$C_{10}$ cycloalkylalkyl means cyclopropylmethyl through cyclononylmethyl or cyclopropylheptyl.

Preferred for reasons of greater ease of synthesis and/or greater herbicidal efficacy are:

(1) Compounds of Formula I where Q is $Q_1$.

(2) Compounds of Formula I where Q is $Q_2$ or $Q_3$.

(3) Compounds of Preferred 1 where
W is O;
R is H; and
the carbon of $R_4$ bonded to $W_1$ is also bonded to at least one hydrogen.

(4) Compounds of Preferred 3 where
X is $CH_3$, $OCH_3$, $OC_2H_5$, Cl, Br, F, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $CH_2SC_2H_5$, cyclopropyl,

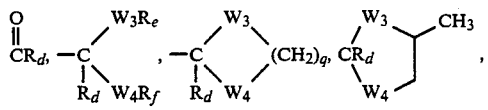

$OCF_2H$, $SCF_2H$, $C\equiv CH$ or $C\equiv CCH_3$.

(5) Compounds of Preferred 4 where
$R_4$ is $C_1$-$C_4$ alkyl, $C_3$-$C_4$ alkenyl, $C_3$-$C_4$ alkynyl, $C_2$-$C_4$ alkyl substituted with 1-3 substituents selected from 0-3 atoms of F or Cl, 0-2 $OCH_3$ or 0-1 CN, or $C_3$-$C_4$ alkenyl substituted with 1-3 Cl.

(6) Compounds of Preferred 5 where
$R_2$ is H; and
$R_1$ is in the 5-position and selected from H, F, Cl, Br, $C_1$-$C_2$ alkyl, $C_1$-$C_3$ alkoxy or $C_1$-$C_3$ alkylthio.

(7) Compounds of Preferred 6 where
A is A-1;
X is $CH_3$, $OCH_3$, $OC_2H_5$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

(8) Compounds of Preferred 7 where
$R_1$ is H, Cl, $CH_3$ or $OCH_3$;
n is O; and
E is a single bond.

(9) Compounds of Preferred 8 where
$R_4$ is $C_1$-$C_3$ alkyl, $CH_2CH=CH_2$, $CH_2C\equiv CH$, $CH_2CH_2Cl$ or $CH_2CH_2OCH_3$.

(10) Compounds of Preferred 9 where
Q is $-C(S)W_1R_4$; and
$W_1$ is S.

(11) Compounds of Preferred 9 where
Q is $-C(S)W_1R_4$; and
$W_1$ is O.

(12) Compounds of Preferred 10 where J is J-1.
(13) Compounds of Preferred 10 where J is J-2.
(14) Compounds of Preferred 10 where J is J-3.
(17) Compounds of Preferred 10 where J is J-6.
(18) Compounds of Preferred 10 where J is J-7.
(19) Compounds of Preferred 10 where J is J-8.
(20) Compounds of Preferred 10 where J is J-9.
(21) Compounds of Preferred 10 where J is J-10.
(22) Compounds of Preferred 10 where J is J-11.
(23) Compounds of Preferred 10 where J is J-12.
(24) Compounds of Preferred 11 where J is J-1.
(25) Compounds of Preferred 11 where J is J-2.
(26) Compounds of Preferred 11 where J is J-3.
(27) Compounds of Preferred 11 where J is J-4.
(28) Compounds of Preferred 11 where J is J-5.
(29) Compounds of Preferred 11 where J is J-6.
(30) Compounds of Preferred 11 where J is J-7.
(31) Compounds of Preferred 11 where J is J-8.

(32) Compounds of Preferred 11 where J is J-9.
(33) Compounds of Preferred 11 where J is J-10.
(34) Compounds of Preferred 11 where J is J-11.
(35) Compounds of Preferred 11 where J is J-12.
(36) Compounds of Preferred 2 where
W is O;
R is H; and
is other than $C(CH_3)_3$.
(37) Compounds of Preferred 36 where
X is $CH_3$, $OCH_3$, $OC_2H_5$, Cl, Br, F, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $CH_2SC_2H_5$, cyclopropyl,

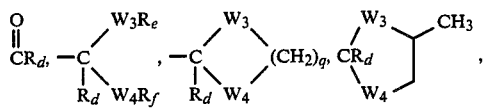

$OCF_2H$, $SCF_2H$, $C\equiv CH$ or $C\equiv CCH_3$.
(38) Compounds of Preferred 37 where
$R_{15}$ is H, $C_1$-$C_3$ alkyl, $C_3$-$C_4$ alkenyl or $C_3$-$C_4$ alkynyl;
$R_{16}$ is H, $C_1$-$C_3$ alkyl or $CH_2CH=CH_2$, or
$R_{15}$ and $R_{16}$ are taken together to form $(CH_2)_4$, $(CH_2)_5$ or $CH_2CH_2OCH_2CH_2$.
(39) Compounds of Preferred 38 where
$R_2$ is H; and
$R_1$ is in the 5-position and selected from H, F, Cl, Br, $C_1$-$C_2$alkyl, $C$-$C_3$ alkoxy or $C_1$-$C_3$ alkylthio.
(40) Compounds of Preferred 39 where
A is A-1;
X is $CH_3$, $OCH_3OC_2H_5$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$
(41) Compounds of Preferred 40 where
$R_1$ is H, Cl, $CH_3$ or $OCH_3$;
n is O; and
E is a single bond.
(42) Compounds of Preferred 41 where
$R_{13}$ is $C_1$-$C_2$ alkyl:
$R_{14}$ is $C_1$-$C_2$ alkyl;
$R_{15}$ is H or $C_1$-$C_3$ alkyl; and
$R_{16}$ is H or $C_1$-$C_3$ alkyl.
(43) Compounds of Preferred 42 where
Q is $-C(S)NR_{15}R_{16}$.
(44) Compounds of Preferred 42 where
Q is $-C(=NR_{13})W_1R_{14}$.
(45) Compounds of Preferred 43 where J is J-1.
(46) Compounds of Preferred 43 where J is J-2.
(47) Compounds of Preferred 43 where J is J-3.
(48) Compounds of Preferred 43 where J is J-4.
(49) Compounds of Preferred 43 where J is J-5.
(50) Compounds of Preferred 43 where J is J-6.
(51) Compounds of Preferred 43 where J is J-7.
(52) Compounds of Preferred 43 where J is J-8.
(53) Compounds of Preferred 43 where J is J-9.
(54) Compounds of Preferred 43 where J is J-10.
(55) Compounds of Preferred 43 where J is J-11.
(56) Compounds of Preferred 43 where J is J-12.
(57) Compounds of Preferred 44 where J is J-1.
(58) Compounds of Preferred 44 where J is J-2.
(59) Compounds of Preferred 44 where J is J-3.
(60) Compounds of Preferred 44 where J is J-4.
(61) Compounds of Preferred 44 where J is J-5.
(62) Compounds of Preferred 44 where J is J-6.
(63) Compounds of Preferred 44 where J is J-7.
(64) Compounds of Preferred 44 where J is J-8.
(65) Compounds of Preferred 44 where J is J-9.
(66) Compounds of Preferred 44 where J is J-10.
(67) Compounds of Preferred 44 where J is J-11.
(68) Compounds of Preferred 44 where J is J-12.

Specifically preferred for reasons of their highest herbicidal activity, greatest plant growth regulant activity and/or most favorable ease of synthesis are:

N-[(4,6-dimethoxypyrimidin-2-yl)aminocarbonyl]-2-(1-pyrrolidinylthioxomethyl)benzenesulfonamide, m.p. 184° C.; and 2-[[(4,6-dimethoxypyrimidin-2-yl)aminocarbonyl]aminosulfonyl]-N,N-dimethylbenzenecarbothioamide, m.p. 191° C.(d).

DETAILED DESCRIPTION OF THE INVENTION

Compounds of Formula I can be prepared by one or more of the methods shown below.

Equation 1

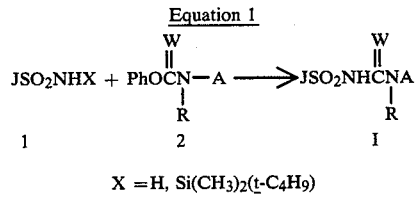

$X = H, Si(CH_3)_2(t\text{-}C_4H_9)$

When X is H, the methods described in U.S. Pat. No. 4,443,245 are employed. Where X is $Si(CH_3)_2(\text{---}C_4H_9)$, one equivalent of a source of fluoride ion, such as tetrabutylammonium fluoride, is used to promote the reaction.

Equation 2

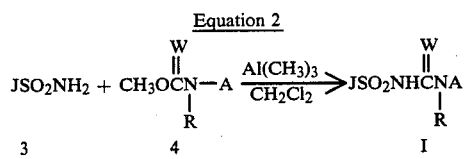

The reaction Equation 2 is described in U.S. Pat. No. 4,398,939.

Compounds of Formula 1, where J is as previously described and Q contains the dithioester group can be prepared from the corresponding carboxylic acids by treatment with certain O/S exchange reagents as described by M. Yokoyama, Y. Hasegawa, H. Katanaka, Y. Kawazoe, and T. Imamoto, *Synthesis* 827 (1984), and U. Pedersen, B. Yde, N. M. Yousif and S.-O. Lawesson, *Sulfur Letters* 2, 167 (1983). An example of this reaction is shown in Equation 3.

Equation 3

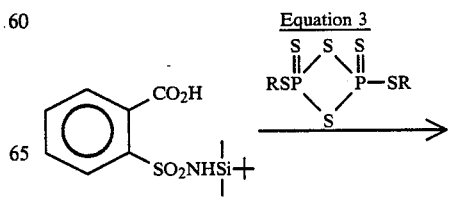

-continued
Equation 3

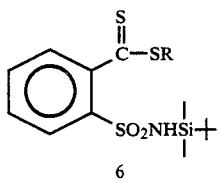

Compounds of Formula 1 where J is previously described and Q contains the thioamide group can be prepared by reaction of the corresponding carboxamide with certain O/S exchange reagents described by B. Yde, N. M. Yousif, U. Pedersen, I. Thomsen, and S.-O. Lawesson, *Tetrahedron*, 40, 2047 (1984).

Alternatively, the thioamide group can be prepared by following the metallation procedure of Equation 4 and quenching the organometallic with an aryl or alkyl isothiocyanate.

Equation 4

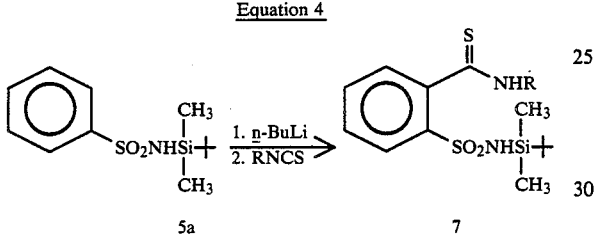

Compounds of Formula 1 where J is as previously described and Q contains the thionoester group can be prepared by reaction of the corresponding ester with certain O/S exchange reagents described by R. S. Pedersen, S. Scheibye, K. Clausen, and S. -O. Lawesson, *Bull. Soc. Chim. Belg.* 87, 293 (1978).

Compounds of Formula 1 where J is as previously described and Q is Q₃ can be prepared by metallation of the corresponding sulfonamide derivative, quenching the organometallic with a $C_1$–$C_4$ alkyl (isocyanate or) isothiocyanate and reaction of the anionic intermediate with a $C_1$–$C_4$ alkylating agent as shown in Equation 5.

Equation 5

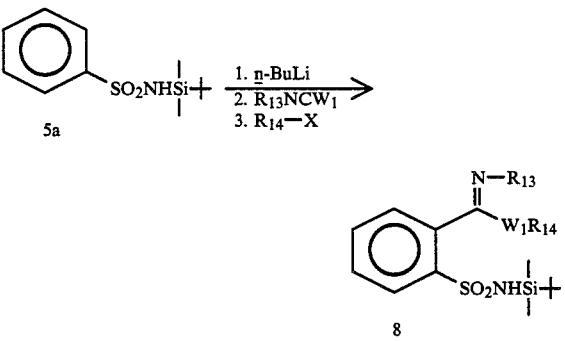

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The preparation of the compounds of the invention is further illustrated by the following examples.

EXAMPLE 1

N-[(4,6-dimethoxypyrimidin-2-yl)aminocarbonyl]-2-[(2,5-dihydro-1H-pyrrol-1-yl)thioxocarbonyl]benzenesulfonamide To a solution of 2-[(1-pyrrolidinyl)thioxomethyl]benzenesulfonamide (0.7 g) and phenyl 4,6-(dimethoxypyrimidin-2-yl)carbamate (0.78 g) in acetonitrile (50 ml) was added 1,8-diazabicyclo[5.4.0]undec-7-ene (0.42 mL). After the mixture had been stirred for 18 hours at ambient temperature, an addition of water was made (100 mL) followed by acetic acid (1 mL). The precipitate was filtered and dried. The crude product (1.09 g) was recrystallized from ether (0.86 g. m.p. 184° C. 73.5% yield);

IR: 3400 cm⁻¹, 3300 cm⁻¹, 1700 cm⁻¹:

NMR: 2.0 ppm, m, 4H; 3.3 ppm, m, 1H; 3.4 ppm, m, 1H; 3.7 ppm, m, 1H; 3.8 ppm, m, 1H; 3.9, s, 6H; 5.8 ppm, s, 1H; 7.2 ppm, dxd, 1H; 7.5 ppm, m, 2H, 8.3 ppm, d, 1H.

EXAMPLE 2

2-[(1-pyrrolidinyl)thioxomethyl]benzenesulfonamide

To a solution of 2-(1-pyrrolidinyl)carbonylbenzenesulfonamide (5.0 g) in 1,2-dimethoxyethane (100 mL) was added 2,4-bis(4'-methoxyphenyl)-1,3,2,4-dithiaphosphetane 2,4-disulfide (Lawesson's Reagent). The slurry was heated at reflux for 2 hours under a nitrogen atmosphere. Flash chromatography of the reaction mixture on silica gel (hexane:ethyl acetate, 2:1) gave the purified product (1.88 g, m.p. 186°–7° C.);

IR: 3200 cm⁻¹3100 cm⁻¹;

NMR (CDCl₃): 2.0 ppm, m, 4H; 3.3 ppm, t, 2H; 3.9 ppm, t, 2H; 6.7 ppm, s, 2H; 7.3 ppm, dxd, 1H; 7.5 ppm, m, 2H; 8.0 ppm, dxd, 1H.

EXAMPLE 3

N-[(Dimethyl)(1,1-dimethylethyl)silyl]-2-[(1-methylamino)thioxomethyl]benzenesulfonamide To a solution of N-[(dimethyl)(1,1-dimethylethyl)-silyl]benzenesulfonamide (13.57 g) in dimethoxyethane (100 mL) at −78° C. was added dropwise n-butyl lithium (1.6 M, 68.75 mL). The resulting solution was stirred at −20° C. for 30 minutes and then recooled to −78° C. and treated with a solution of methylisothiocyanate (5.13 mL) in dimethoxyethane (6 mL). The resulting solution was stirred at −40° C. for 4 hours. Isolation was by aqueous work-up and purification by flash chromatography (30% ethyl acetate, 70% hexane) to yield 4.65 g of product.

NMR: 10.7 ppm, bs, 1H: 7.85 ppm, d, 1H; 7.58 ppm, m, 2H; 7.28 ppm, d, 1H; 6.87 ppm, s, 1H; 3.1 ppm, d, 3H; 0.85 ppm, s, 9H; 0.13 ppm, s, 6H.

EXAMPLE 4

2-[((4,6-Dimethoxypyrimidin-2-yl)aminocarbonyl)aminosulfonyl]benzenecarboximidothioic acid. N,S-diethylester To a solution of phenyl 4,6-(dimethoxypyrimidin-2-yl)carbamate (0.71 g) and N-[(1.1-dimethylethyl)silyl]-2-[N,S-diethylcarboximidothioate](1.0 g) in acetonitrile (25 mL) was added to tetra-n-butylammonium fluoride trihydrate (0.82 g). After the mixture had been stirred for one hour at 25° C., aqueous work-up and purification by chromatography gave 0.34 g of product: m.p. 165°-167° C.

IR (Nujol) 1710 cm$^{-1}$;

NMR: 12.75 ppm, bs, 1H; 12.4 ppm, bs, 1H; 8.38 ppm, dxd, 1H; 7.6 ppm, m, 2H; 7.2 ppm, d, 1H; 5.78 ppm, s, 1H; 3.93 ppm, s, 6H: 3.4 ppm, m, 2H; 2.5 ppm, q, 2H; 1.13 ppm, dxt, 6H.

EXAMPLE 5

N-[(Dimethyl)(1,1-dimethylethyl)silyl]-2-[N,S-diethylcarboximidothioate]benzenesulfonamide To a solution of N-[(dimethyl)(1,1-dimethylethyl)silyl]benzenesulfonamide (13.57 g) in dimethoxyethane at −78° C. was added dropwise a solution of n-butyllithium (1.6M, 70.9 mL) in dimethoxyethane (100 mL). The reaction was stirred at −30° C. for 30 minutes and recooled to −78° C. and treated dropwise with a solution of ethyl isothiocyanate (6.56 mL) in dimethoxyethane (15 mL). The reaction was stirred at −30° C. for 4 hours and recooled to −78° C. and treated with a solution of ethyl iodide (b 6 mL) in dimethoxyethane (15 mL). The reaction was allowed to warm to 25° C. and stir for 18 hours. Aqueous work-up and purification by flash chromatography (10% ethyl acetate, 90% hexane) gave 8.3 g of the oily product.

NMR: 8.01 ppm, d, 1H; 7.52 ppm, m, 3H; 6.25 ppm, bs, 1H: 3.65 ppm, q, 2H; 2.5 ppm, q, 2H; 1.37 ppm, t, 3H; 1.13 ppm, t, 3H; 0.90 ppm, s, 9H; 0.195 ppm, s, 6H.

By applying the procedures described above, one skilled in the art can prepare the compounds listed in Tables I-XIII.

TABLE I

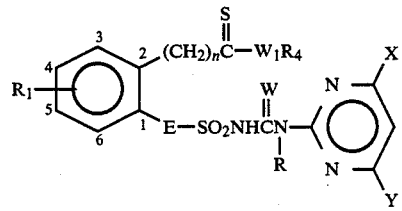

| n | R | $R_1$ | W | $W_1$ | E | $R_4$ | X | Y | m.p. (°C.) |
|---|---|---|---|---|---|---|---|---|---|
| 0 | H | H | O | S | — | $CH_3$ | $CH_3$ | $CH_3$ | |
| 0 | H | H | O | S | — | $CH_3$ | $CH_3$ | $OCH_3$ | |
| 0 | H | H | O | S | — | $CH_3$ | $OCH_3$ | $OCH_3$ | |
| 0 | H | H | O | S | — | $CH_3$ | Cl | $OCH_3$ | |
| 0 | H | H | O | S | — | $CH_3$ | $CH_3$ | $OCH_2CH=CH_2$ | |
| 0 | H | H | O | S | — | $CH_3$ | $OCF_2H$ | $CH_3$ | |
| 0 | H | H | O | S | — | $CH_3$ | $OCH_2OCH_3$ | $CH_3$ | |
| 0 | H | H | O | S | — | $CH_3$ | $OCH_3$ | $N(CH_3)_2$ | |
| 0 | H | H | O | S | — | $CH_3$ | $CH_3$ | $CH(OCH_3)_2$ | |
| 0 | H | H | O | S | — | $CH_3$ | $OC_2H_5$ | $CH_3$ | |
| 0 | H | H | O | S | — | $CH_3$ | $OCH_3$ | $NHCH_3$ | |
| 0 | H | H | O | S | — | $CH_3$ | $CH_3$ | $SCH_3$ | |
| 0 | H | H | O | S | — | $CH_3$ | $CH_3$ | $C\equiv CH$ | |
| 0 | H | H | O | S | — | $CH_3$ | $CH_3$ | $CHSCH_3$ | |
| 0 | H | H | O | S | — | $CH_3$ | $CH_3$ | $SCF_2H$ | |
| 0 | H | H | O | S | — | $CH_3$ | $OCH_3$ | $N(OCH_3)CH_3$ | |
| 0 | H | H | O | S | — | $CH_3$ | $CH_3$ | $OCH_2C\equiv CH$ | |
| 0 | H | 5-Cl | O | S | — | $CH_3$ | $OCH_3$ | $OCH_3$ | |
| 0 | H | 5-$OCH_3$ | O | S | — | $CH_3$ | $OCH_3$ | $OCH_3$ | |
| 0 | H | 5-$SCH_3$ | O | S | — | $CH_3$ | $OCH_3$ | $OCH_3$ | |
| 0 | $CH_3$ | H | O | S | — | $CH_3$ | $OCH_3$ | $OCH_3$ | |
| 0 | H | H | S | S | — | $CH_3$ | $OCH_3$ | $OCH_3$ | |
| 0 | H | H | O | S | —$CH_2$— | $CH_3$ | $OCH_3$ | $OCH_3$ | |
| 0 | H | H | O | S | — | —$CH_2CH=CH_2$ | $CH_3$ | $OCH_3$ | |
| 0 | H | H | O | S | — | —$CH_2CH=CH_2$ | $OCH_3$ | $OCH_3$ | |
| 0 | H | H | O | S | — | $CH_2C_6H_5$ | $CH_3$ | $OCH_3$ | |
| 0 | H | 5-$NH_2$ | O | S | — | $CH_3$ | $OCH_3$ | $OCH_3$ | |
| 0 | H | 5-$NHCH_3$ | O | S | — | $CH_3$ | $OCH_3$ | $OCH_3$ | |
| 0 | H | 5-$N(CH_3)_2$ | O | S | — | $CH_3$ | $OCH_3$ | $OCH_3$ | |
| 0 | H | H | O | S | — | $CH_2C_6H_5$ | $OCH_3$ | $OCH_3$ | |
| 0 | H | H | O | S | — | $C_6H_5$ | $CH_3$ | $OCH_3$ | |
| 0 | H | H | O | S | — | $C_6H_5$ | $OCH_3$ | $OCH_3$ | |
| 0 | H | H | O | S | — | p-$ClC_6H_5$ | $CH_3$ | $OCH_3$ | |
| 0 | H | H | O | S | — | p-$ClC_6H_5$ | $OCH_3$ | $OCH_3$ | |
| 0 | H | H | O | S | — | $CH_2OCH_3$ | $OCH_3$ | $OCH_3$ | |
| 0 | H | H | O | S | — | $CH_2CH_2CN$ | $OCH_3$ | $OCH_3$ | |

TABLE I-continued

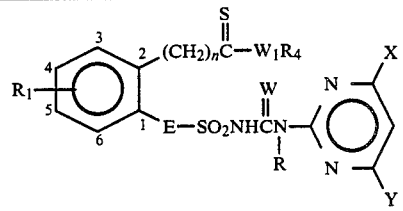

| n | R | R₁ | W | W₁ | E | R₄ | X | Y | m.p. (°C.) |
|---|---|---|---|---|---|---|---|---|---|
| 0 | H | H | O | S | — | CH₂C≡CH | OCH₃ | OCH₃ | |
| 0 | H | H | O | O | — | CH₃ | CH₃ | CH₃ | |
| 0 | H | H | O | O | — | CH₃ | CH₃ | OCH₃ | |
| 0 | H | H | O | O | — | CH₃ | OCH₃ | OCH₃ | |
| 0 | H | H | O | O | — | CH₃ | Cl | OCH₃ | |
| 0 | H | H | O | O | — | CH(CH₃)₂ | OCH₃ | OCH₃ | |
| 0 | H | H | O | O | — | CH₂CH₂OCH₃ | OCH₃ | OCH₃ | |
| 0 | H | H | O | O | — | C₆H₅ | OCH₃ | OCH₃ | |
| 0 | H | H | O | O | — | C₂H₅ | OCH₃ | OCH₃ | |
| 0 | H | H | O | O | — | CH₂C₆H₅ | OCH₃ | OCH₃ | |
| 0 | H | 5-Cl | O | O | — | CH₃ | OCH₃ | OCH₃ | |
| 0 | H | 5-OCH₃ | O | O | — | CH₃ | OCH₃ | OCH₃ | |
| 0 | H | 5-SCH₃ | O | O | — | CH₃ | OCH₃ | OCH₃ | |
| 0 | CH₃ | H | O | O | — | CH₃ | OCH₃ | OCH₃ | |
| 0 | H | H | S | O | — | CH₃ | OCH₃ | OCH₃ | |
| 0 | H | H | O | O | —CH₂— | CH₃ | OCH₃ | OCH₃ | |
| 1 | H | H | O | S | — | CH₃ | CH₃ | OCH₃ | |
| 1 | H | H | O | S | — | CH₃ | OCH₃ | OCH₃ | |
| 1 | H | H | O | S | — | CH₃ | Cl | OCH₃ | |

TABLE II

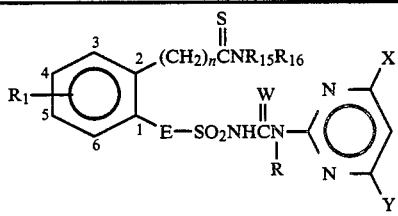

| n | R | R₁ | W | E | R₁₅ | R₁₆ | X | Y | m.p. (°C.) |
|---|---|---|---|---|---|---|---|---|---|
| 0 | H | H | O | — | CH₃ | CH₃ | CH₃ | CH₃ | |
| 0 | H | H | O | — | CH₃ | CH₃ | CH₃ | OCH₃ | |
| 0 | H | H | O | — | CH₃ | CH₃ | OCH₃ | OCH₃ | 191 |
| 0 | H | H | O | — | CH₃ | CH₃ | Cl | OCH₃ | |
| 0 | H | H | O | — | —(CH₂)₄— | | CH₃ | CH₃ | |
| 0 | H | H | O | — | —(CH₂)₄— | | OCH₃ | CH₃ | |
| 0 | H | H | O | — | —(CH₂)₄— | | OCH₃ | OCH₃ | 184 |
| 0 | H | H | O | — | —(CH₂)₄— | | Cl | OCH₃ | |
| 0 | H | H | O | — | H | H | CH₃ | CH₃ | |
| 0 | H | H | O | — | H | H | OCH₃ | OCH₃ | |
| 0 | H | H | O | — | H | H | Cl | OCH₃ | |
| 0 | H | H | O | — | H | CH₃ | Cl | OCH₃ | 239–242 |
| 0 | H | H | O | — | H | CH₃ | CH₃ | CH₃ | 177–179 |
| 0 | H | H | O | — | H | CH₃ | CH₃ | OCH₃ | 188–190 |
| 0 | H | H | O | — | H | CH₃ | OCH₃ | OCH₃ | 173–175 |
| 0 | H | H | O | — | H | CH₂CH=CH₂ | OCH₃ | OCH₃ | |
| 0 | H | H | O | — | H | C₆H₅ | OCH₃ | OCH₃ | |
| 0 | H | H | O | — | H | p-ClC₆H₄ | OCH₃ | OCH₃ | |
| 0 | H | H | O | — | H | p-CH₃OC₆H₄ | OCH₃ | OCH₃ | |
| 0 | H | H | O | — | —(CH₂CH₂OCH₂CH₂)— | | CH₃ | CH₃ | |
| 0 | H | H | O | — | —(CH₂CH₂OCH₂CH₂)— | | CH₃ | OCH₃ | |
| 0 | H | H | O | — | —(CH₂CH₂OCH₂CH₂)— | | OCH₃ | OCH₃ | |
| 0 | H | H | O | — | H | CH(CH₃)₂ | OCH₃ | OCH₃ | |
| 0 | H | H | O | — | H | C(CH₃)₃ | OCH₃ | OCH₃ | |
| 0 | H | H | O | — | CH₃ | CH₃ | CH₃ | OCH₂CH=CH₂ | |
| 0 | H | H | O | — | CH₃ | CH₃ | OCF₂H | CH₃ | |
| 0 | H | 5-NH₂ | O | — | CH₃ | CH₃ | OCH₃ | OCH₃ | |
| 0 | H | 5-NHCH₃ | O | — | CH₃ | CH₃ | OCH₃ | OCH₃ | |
| 0 | H | 5-N(CH₃)₂ | O | — | CH₃ | CH₃ | OCH₃ | OCH₃ | |
| 0 | H | H | O | — | CH₃ | CH₃ | OCH₂OCH₃ | CH₃ | |
| 0 | H | H | O | — | CH₃ | CH₃ | OCH₃ | N(CH₃)₂ | |
| 0 | H | H | O | — | CH₃ | CH₃ | CH₃ | CH(OCH₃)₂ | |
| 0 | H | H | O | — | CH₃ | CH₃ | OC₂H₅ | CH₃ | |
| 0 | H | H | O | — | CH₃ | CH₃ | OCH₃ | NHCH₃ | |

TABLE II-continued

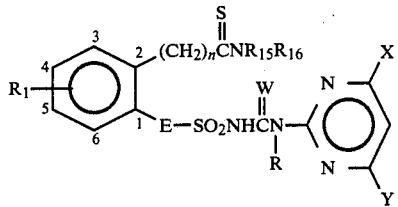

| n | R | R₁ | W | E | R₁₅ | R₁₆ | X | Y | m.p. (°C.) |
|---|---|---|---|---|---|---|---|---|---|
| 0 | H | H | O | — | CH₃ | CH₃ | CH₃ | SCH₃ | |
| 0 | H | H | O | — | CH₃ | CH₃ | CH₃ | —C≡CH | |
| 0 | H | H | O | — | CH₃ | CH₃ | CH₃ | CH₂SCH₃ | |
| 0 | H | H | O | — | CH₃ | CH₃ | CH₃ | SCF₂H | |
| 0 | H | H | O | — | CH₃ | CH₃ | OCH₃ | N(OCH₃)CH₃ | |
| 0 | H | H | O | — | CH₃ | CH₃ | CH₃ | OCH₂C≡CH | |
| 0 | CH₃ | H | O | — | CH₃ | CH₃ | OCH₃ | OCH₃ | |
| 0 | H | 5-Cl | O | — | CH₃ | CH₃ | OCH₃ | OCH₃ | |
| 0 | H | 5-OCH₃ | O | — | CH₃ | CH₃ | OCH₃ | OCH₃ | |
| 0 | H | 5-SCH₃ | O | — | CH₃ | CH₃ | OCH₃ | OCH₃ | |
| 0 | H | H | S | — | CH₃ | CH₃ | OCH₃ | OCH₃ | |
| 0 | H | H | O | —CH₂— | CH₃ | CH₃ | OCH₃ | OCH₃ | |
| 0 | H | H | O | — | CH₃ | CH₃ | OCH₃ | OCH₃ | |
| 1 | H | H | O | — | CH₃ | CH₃ | OCH₃ | OCH₃ | |
| 1 | H | H | O | — | CH₃ | CH₃ | CH₃ | OCH₃ | |
| 1 | H | H | O | — | CH₃ | CH₃ | CH₃ | CH₃ | |
| 1 | H | H | O | — | CH₃ | CH₃ | Cl | OCH₃ | |
| 0 | H | H | O | — | H | CH₂CH₃ | OCH₃ | OCH₃ | 169–171 |
| 0 | H | H | O | — | H | CH₂CH₃ | CH₃ | CH₃ | >208 |
| 0 | H | H | O | — | H | CH₂CH₃ | CH₃ | OCH₃ | 167–169 |
| 0 | H | H | O | — | H | CH₂CH₃ | Cl | OCH₃ | 204–206 |
| 0 | H | H | O | — | H | (CH₂)₃OCH₃ | CH₃ | CH₃ | 144–146 |
| 0 | H | H | O | — | H | (CH₂)₃OCH₃ | OCH₃ | OCH₃ | 155–157 |
| 0 | H | H | O | — | H | (CH₂)₃OCH₃ | Cl | OCH₃ | 149–151 |

TABLE III

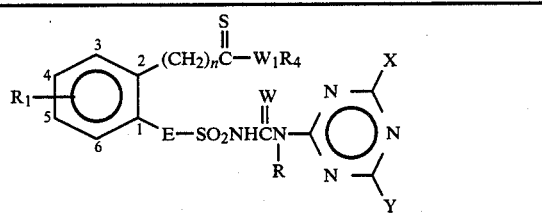

| n | R | R₁ | W | W₁ | E | R₄ | X | Y | m.p. (°C.) |
|---|---|---|---|---|---|---|---|---|---|
| 0 | H | H | O | S | — | CH₃ | CH₃ | CH₃ | |
| 0 | H | H | O | S | — | CH₃ | CH₃ | OCH₃ | |
| 0 | H | H | O | S | — | CH₃ | OCH₃ | OCH₃ | |
| 0 | H | H | O | S | — | CH₃ | Cl | OCH₃ | |
| 0 | H | H | O | S | — | CH₃ | CH₃ | OCH₂CH=CH₂ | |
| 0 | H | H | O | S | — | CH₃ | OCF₂H | CH₃ | |
| 0 | H | H | O | S | — | CH₃ | OCH₂OCH₃ | CH₃ | |
| 0 | H | H | O | S | — | CH₃ | OCH₃ | N(CH₃)₂ | |
| 0 | H | H | O | S | — | CH₃ | CH₃ | CH(OCH₃)₂ | |
| 0 | H | H | O | S | — | CH₃ | OC₂H₅ | CH₃ | |
| 0 | H | H | O | S | — | CH₃ | OCH₃ | NHCH₃ | |
| 0 | H | H | O | S | — | CH₃ | CH₃ | SCH₃ | |
| 0 | H | H | O | S | — | CH₃ | CH₃ | C≡CH | |
| 0 | H | H | O | S | — | CH₃ | CH₃ | CHSCH₃ | |
| 0 | H | H | O | S | — | CH₃ | CH₃ | SCF₂H | |
| 0 | H | H | O | S | — | CH₃ | OCH₃ | N(OCH₃)CH₃ | |
| 0 | H | H | O | S | — | CH₃ | CH₃ | OCH₂C≡CH | |
| 0 | H | 5-Cl | O | S | — | CH₃ | OCH₃ | OCH₃ | |
| 0 | H | 5-OCH₃ | O | S | — | CH₃ | OCH₃ | OCH₃ | |
| 0 | H | 5-SCH₃ | O | S | — | CH₃ | OCH₃ | OCH₃ | |
| 0 | CH₃ | H | O | S | — | CH₃ | OCH₃ | OCH₃ | |
| 0 | H | H | S | S | — | CH₃ | OCH₃ | OCH₃ | |
| 0 | H | H | O | S | —CH₂— | CH₃ | OCH₃ | OCH₃ | |
| 0 | H | H | O | S | — | —CH₂CH=CH₂ | CH₃ | OCH₃ | |
| 0 | H | H | O | S | — | —CH₂CH=CH₂ | OCH₃ | OCH₃ | |
| 0 | H | H | O | S | — | CH₂C₆H₅ | CH₃ | OCH₃ | |
| 0 | H | 5-NH₂ | O | S | — | CH₃ | CH₃ | OCH₃ | |
| 0 | H | 5-NHCH₃ | O | S | — | CH₃ | CH₃ | OCH₃ | |
| 0 | H | 5-N(CH₃)₂ | O | S | — | CH₃ | CH₃ | OCH₃ | |
| 0 | H | H | O | S | — | CH₂C₆H₅ | OCH₃ | OCH₃ | |

TABLE III-continued

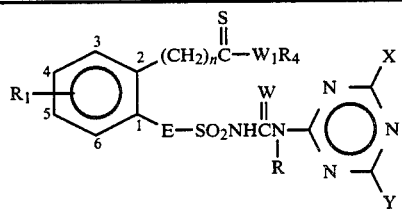

| n | R | R₁ | W | W₁ | E | R₄ | X | Y | m.p. (°C.) |
|---|---|---|---|---|---|---|---|---|---|
| 0 | H | H | O | S | — | C₆H₅ | CH₃ | OCH₃ | |
| 0 | H | H | O | S | — | C₆H₅ | OCH₃ | OCH₃ | |
| 0 | H | H | O | S | — | p-ClC₆H₄ | CH₃ | OCH₃ | |
| 0 | H | H | O | S | — | p-ClC₆H₄ | OCH₃ | OCH₃ | |
| 0 | H | H | O | S | — | CH₂OCH₃ | OCH₃ | OCH₃ | |
| 0 | H | H | O | S | — | CH₂CH₂CN | OCH₃ | OCH₃ | |
| 0 | H | H | O | S | — | CH₂C≡CH | OCH₃ | OCH₃ | |
| 0 | H | H | O | O | — | CH₃ | CH₃ | CH₃ | |
| 0 | H | H | O | O | — | CH₃ | CH₃ | OCH₃ | |
| 0 | H | H | O | O | — | CH₃ | OCH₃ | OCH₃ | |
| 0 | H | H | O | O | — | CH₃ | Cl | OCH₃ | |
| 0 | H | H | O | O | — | CH(CH₃)₂ | OCH₃ | OCH₃ | |
| 0 | H | H | O | O | — | CH₂CH₂OCH₃ | OCH₃ | OCH₃ | |
| 0 | H | H | O | O | — | C₆H₅ | OCH₃ | OCH₃ | |
| 0 | H | H | O | O | — | C₂H₅ | OCH₃ | OCH₃ | |
| 0 | H | H | O | O | — | CH₂C₆H₅ | OCH₃ | OCH₃ | |
| 0 | H | 5-Cl | O | O | — | CH₃ | OCH₃ | OCH₃ | |
| 0 | H | 5-OCH₃ | O | O | — | CH₃ | OCH₃ | OCH₃ | |
| 0 | H | 5-SCH₃ | O | O | — | CH₃ | OCH₃ | OCH₃ | |
| 0 | CH₃ | H | O | O | — | CH₃ | OCH₃ | OCH₃ | |
| 0 | H | H | S | O | — | CH₃ | OCH₃ | OCH₃ | |
| 0 | H | H | O | O | —CH₂— | CH₃ | OCH₃ | OCH₃ | |
| 1 | H | H | O | S | — | CH₃ | CH₃ | OCH₃ | |
| 1 | H | H | O | S | — | CH₃ | OCH₃ | OCH₃ | |
| 1 | H | H | O | S | — | CH₃ | Cl | OCH₃ | |

TABLE IV

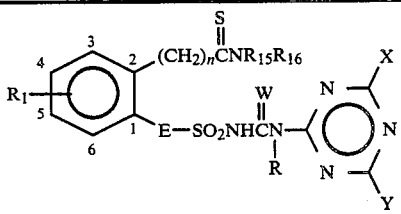

| n | R | R₁ | W | E | R₁₅ | R₁₆ | X | Y | m.p. (°C.) |
|---|---|---|---|---|---|---|---|---|---|
| 0 | H | H | O | — | CH₃ | CH₃ | CH₃ | CH₃ | |
| 0 | H | H | O | — | CH₃ | CH₃ | CH₃ | OCH₃ | |
| 0 | H | H | O | — | CH₃ | CH₃ | OCH₃ | OCH₃ | |
| 0 | H | H | O | — | CH₃ | CH₃ | Cl | OCH₃ | |
| 0 | H | H | O | — | —(CH₂)₄— | | CH₃ | CH₃ | |
| 0 | H | H | O | — | —(CH₂)₄— | | OCH₃ | CH₃ | |
| 0 | H | H | O | — | —(CH₂)₄— | | OCH₃ | OCH₃ | 153–155 |
| 0 | H | H | O | — | —(CH₂)₄— | | Cl | OCH₃ | |
| 0 | H | H | O | — | H | H | CH₃ | CH₃ | |
| 0 | H | H | O | — | H | H | CH₃ | OCH₃ | |
| 0 | H | H | O | — | H | H | OCH₃ | OCH₃ | |
| 0 | H | H | O | — | H | H | Cl | OCH₃ | |
| 0 | H | H | O | — | H | CH₃ | CH₃ | CH₃ | |
| 0 | H | H | O | — | H | CH₃ | CH₃ | OCH₃ | |
| 0 | H | H | O | — | H | CH₃ | OCH₃ | OCH₃ | 168–170 |
| 0 | H | H | O | — | H | CH₂CH=CH₂ | OCH₃ | OCH₃ | |
| 0 | H | H | O | — | H | C₆H₅ | OCH₃ | OCH₃ | |
| 0 | H | H | O | — | H | p-ClC₆H₄ | OCH₃ | OCH₃ | |
| 0 | H | H | O | — | H | p-CH₃OC₆H₄ | OCH₃ | OCH₃ | |
| 0 | H | H | O | — | —(CH₂CH₂OCH₂CH₂)— | | CH₃ | CH₃ | |
| 0 | H | H | O | — | —(CH₂CH₂OCH₂CH₂)— | | CH₃ | OCH₃ | |
| 0 | H | H | O | — | —(CH₂CH₂OCH₂CH₂)— | | OCH₃ | OCH₃ | |
| 0 | H | H | O | — | H | CH(CH₃)₂ | OCH₃ | OCH₃ | |
| 0 | H | H | O | — | H | C(CH₃)₃ | OCH₃ | OCH₃ | |
| 0 | H | H | O | — | CH₃ | CH₃ | CH₃ | OCH₂CH=CH₂ | |
| 0 | H | H | O | — | CH₃ | CH₃ | OCF₂H | CH₃ | |
| 0 | H | 5-NH₂ | O | — | CH₃ | CH₃ | OCH₃ | OCH₃ | |
| 0 | H | 5-NHCH₃ | O | — | CH₃ | CH₃ | OCH₃ | OCH₃ | |
| 0 | H | 5-N(CH₃)₂ | O | — | CH₃ | CH₃ | OCH₃ | OCH₃ | |

TABLE IV-continued

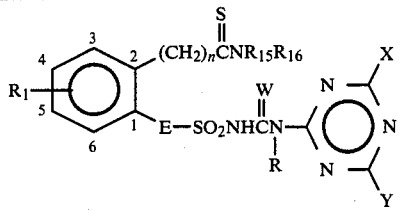

| n | R | R₁ | W | E | R₁₅ | R₁₆ | X | Y | m.p. (°C.) |
|---|---|---|---|---|---|---|---|---|---|
| 0 | H | H | O | — | CH₃ | CH₃ | OCH₂OCH₃ | CH₃ | |
| 0 | H | H | O | — | CH₃ | CH₃ | OCH₃ | N(CH₃)₂ | |
| 0 | H | H | O | — | CH₃ | CH₃ | CH₃ | CH(OCH₃)₂ | |
| 0 | H | H | O | — | CH₃ | CH₃ | OC₂H₅ | CH₃ | |
| 0 | H | H | O | — | CH₃ | CH₃ | OCH₃ | NHCH₃ | |
| 0 | H | H | O | — | CH₃ | CH₃ | CH₃ | SCH₃ | |
| 0 | H | H | O | — | CH₃ | CH₃ | CH₃ | —C≡CH | |
| 0 | H | H | O | — | CH₃ | CH₃ | CH₃ | CH₂SCH₃ | |
| 0 | H | H | O | — | CH₃ | CH₃ | CH₃ | SCF₂H | |
| 0 | H | H | O | — | CH₃ | CH₃ | OCH₃ | N(OCH₃)CH₃ | |
| 0 | H | H | O | — | CH₃ | CH₃ | CH₃ | OCH₂C≡CH | |
| 0 | CH₃ | H | O | — | CH₃ | CH₃ | OCH₃ | OCH₃ | |
| 0 | H | 5-Cl | O | — | CH₃ | CH₃ | OCH₃ | OCH₃ | |
| 0 | H | 5-OCH₃ | O | — | CH₃ | CH₃ | OCH₃ | OCH₃ | |
| 0 | H | 5-SCH₃ | O | — | CH₃ | CH₃ | OCH₃ | OCH₃ | |
| 0 | H | H | S | — | CH₃ | CH₃ | OCH₃ | OCH₃ | |
| 0 | H | H | O | —CH₂— | CH₃ | CH₃ | OCH₃ | OCH₃ | |
| 0 | H | H | O | — | CH₃ | CH₃ | OCH₃ | OCH₃ | |
| 1 | H | H | O | — | CH₃ | CH₃ | OCH₃ | OCH₃ | |
| 1 | H | H | O | — | CH₃ | CH₃ | CH₃ | OCH₃ | |
| 1 | H | H | O | — | CH₃ | CH₃ | CH₃ | CH₃ | |
| 1 | H | H | O | — | CH₃ | CH₃ | Cl | OCH₃ | |
| 0 | H | H | O | — | H | CH₂CH₃ | OCH₃ | OCH₃ | 212–215 |
| 0 | H | H | O | — | H | CH₂CH₃ | CH₃ | OCH₃ | 240–242 |
| 0 | H | H | O | — | H | CH₂CH₃ | CH₃ | CH₃ | |
| 0 | H | H | O | — | H | (CH₂)₃OCH₃ | CH₃ | OCH₃ | 136–138 |
| 0 | H | H | O | — | H | (CH₂)₃OCH₃ | OCH₃ | OCH₃ | 120–123 |
| 0 | H | H | O | — | H | (CH₂)₃OCH₃ | CH₃ | CH₃ | |

TABLE V

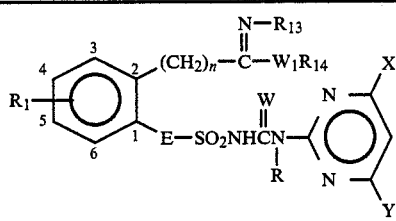

| n | R | R₁ | W | W₁ | E | R₁₃ | R₁₄ | X | Y | m.p. (°C.) |
|---|---|---|---|---|---|---|---|---|---|---|
| 0 | H | H | O | S | — | CH₃ | CH₃ | CH₃ | CH₃ | |
| 0 | H | H | O | S | — | CH₃ | CH₃ | OCH₃ | CH₃ | |
| 0 | H | H | O | S | — | CH₃ | CH₃ | OCH₃ | OCH₃ | |
| 0 | H | H | O | S | — | CH₃ | CH₃ | Cl | OCH₃ | |
| 0 | H | H | O | O | — | C₂H₅ | CH₃ | OCH₃ | OCH₃ | |
| 0 | H | H | O | S | — | CH₃ | C₂H₅ | OCH₃ | OCH₃ | |
| 0 | H | H | O | S | — | C₂H₅ | C₂H₅ | OCH₃ | OCH₃ | 165–167 |
| 0 | H | H | O | S | — | CH₃ | n-C₄H₉ | OCH₃ | OCH₃ | |
| 0 | H | H | O | S | — | n-C₄H₉ | CH₃ | OCH₃ | OCH₃ | |
| 0 | H | H | O | S | — | t-C₄H₉ | CH₃ | OCH₃ | OCH₃ | |
| 0 | H | H | O | O | — | C₂H₅ | C₂H₅ | CH₃ | OCH₃ | |
| 0 | H | H | O | S | — | C₂H₅ | C₂H₅ | CH₃ | CH₃ | |
| 0 | H | 5-N(CH₃) | O | S | — | CH₃ | CH₃ | OCH₃ | OCH₃ | |
| 0 | H | 5-Cl | O | S | — | CH₃ | CH₃ | OCH₃ | OCH₃ | |
| 0 | H | 5-OCH₃ | O | S | — | CH₃ | CH₃ | OCH₃ | OCH₃ | |
| 0 | H | 5-SCH₃ | O | S | — | CH₃ | CH₃ | OCH₃ | OCH₃ | |
| 1 | H | H | O | O | — | CH₃ | CH₃ | OCH₃ | OCH₃ | |
| 0 | CH₃ | H | O | S | — | CH₃ | CH₃ | OCH₃ | OCH₃ | |
| 0 | H | H | S | S | — | CH₃ | CH₃ | OCH₃ | OCH₃ | |
| 0 | H | H | O | S | —CH₂— | CH₃ | CH₃ | OCH₃ | OCH₃ | |
| 0 | H | H | O | S | — | CH₃ | CH₃ | CH₃ | OCH₂CH=CH₂ | |
| 0 | H | H | O | S | — | CH₃ | CH₃ | OCF₂H | CH₃ | |
| 0 | H | H | O | O | — | CH₃ | CH₃ | OCH₂OCH₃ | CH₃ | |
| 0 | H | H | O | S | — | CH₃ | CH₃ | OCH₃ | N(CH₃)₂ | |
| 0 | H | H | O | S | — | CH₃ | CH₃ | CH₃ | CH(OCH₃)₂ | |

TABLE V-continued

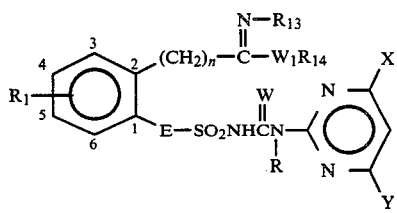

| n | R | $R_1$ | W | $W_1$ | E | $R_{13}$ | $R_{14}$ | X | Y | m.p. (°C.) |
|---|---|---|---|---|---|---|---|---|---|---|
| 0 | H | H | O | S | — | $CH_3$ | $CH_3$ | $OC_2H_5$ | $CH_3$ | |
| 0 | H | H | O | S | — | $CH_3$ | $CH_3$ | $OCH_3$ | $NHCH_3$ | |
| 0 | H | H | O | S | — | $CH_3$ | $CH_3$ | $CH_3$ | $SCH_3$ | |
| 0 | H | H | O | O | — | $CH_3$ | $CH_3$ | $CH_3$ | $-C\equiv CH$ | |
| 0 | H | H | O | S | — | $CH_3$ | $CH_3$ | $CH_3$ | $CHSCH_3$ | |
| 0 | H | H | O | S | — | $CH_3$ | $CH_3$ | $CH_3$ | $SCF_2H$ | |
| 0 | H | H | O | S | — | $CH_3$ | $CH_3$ | $OCH_3$ | $N(OCH_3)CH_3$ | |
| 0 | H | H | O | S | — | $CH_3$ | $CH_3$ | $CH_3$ | $OCH_2C\equiv CH$ | |

TABLE VI

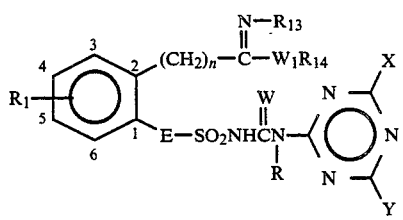

| n | R | $R_1$ | W | $W_1$ | E | $R_{13}$ | $R_{14}$ | X | Y | m.p. (°C.) |
|---|---|---|---|---|---|---|---|---|---|---|
| 0 | H | H | O | S | — | $CH_3$ | $CH_3$ | $CH_3$ | $CH_3$ | |
| 0 | H | H | O | S | — | $CH_3$ | $CH_3$ | $OCH_3$ | $CH_3$ | |
| 0 | H | H | O | S | — | $CH_3$ | $CH_3$ | $OCH_3$ | $OCH_3$ | |
| 0 | H | H | O | S | — | $CH_3$ | $CH_3$ | Cl | $OCH_3$ | |
| 0 | H | H | O | O | — | $C_2H_5$ | $CH_3$ | $OCH_3$ | $OCH_3$ | |
| 0 | H | H | O | S | — | $CH_3$ | $C_2H_5$ | $OCH_3$ | $OCH_3$ | |
| 0 | H | H | O | S | — | $C_2H_5$ | $C_2H_5$ | $OCH_3$ | $OCH_3$ | |
| 0 | H | H | O | S | — | $CH_3$ | n-$C_4H_9$ | $OCH_3$ | $OCH_3$ | |
| 0 | H | H | O | S | — | n-$C_4H_9$ | $CH_3$ | $OCH_3$ | $OCH_3$ | |
| 0 | H | H | O | S | — | t-$C_4H_9$ | $CH_3$ | $OCH_3$ | $OCH_3$ | |
| 0 | H | H | O | O | — | $C_2H_5$ | $C_2H_5$ | $CH_3$ | $OCH_3$ | |
| 0 | H | H | O | S | — | $C_2H_5$ | $C_2H_5$ | $CH_3$ | $CH_3$ | |
| 0 | H | 5-$N(CH_3)$ | O | S | — | $CH_3$ | $CH_3$ | $OCH_3$ | $OCH_3$ | |
| 0 | H | 5-Cl | O | S | — | $CH_3$ | $CH_3$ | $OCH_3$ | $OCH_3$ | |
| 0 | H | 5-$OCH_3$ | O | S | — | $CH_3$ | $CH_3$ | $OCH_3$ | $OCH_3$ | |
| 0 | H | 5-$SCH_3$ | O | S | — | $CH_3$ | $CH_3$ | $OCH_3$ | $OCH_3$ | |
| 1 | H | H | O | O | — | $CH_3$ | $CH_3$ | $OCH_3$ | $OCH_3$ | |
| 0 | $CH_3$ | H | O | S | — | $CH_3$ | $CH_3$ | $OCH_3$ | $OCH_3$ | |
| 0 | H | H | S | S | — | $CH_3$ | $CH_3$ | $OCH_3$ | $OCH_3$ | |
| 0 | H | H | O | S | $-CH_2-$ | $CH_3$ | $CH_3$ | $OCH_3$ | $OCH_3$ | |
| 0 | H | H | O | S | — | $CH_3$ | $CH_3$ | $CH_3$ | $OCH_2CH=CH_2$ | |
| 0 | H | H | O | S | — | $CH_3$ | $CH_3$ | $OCF_2H$ | $CH_3$ | |
| 0 | H | H | O | O | — | $CH_3$ | $CH_3$ | $OCH_2OCH_3$ | $CH_3$ | |
| 0 | H | H | O | S | — | $CH_3$ | $CH_3$ | $OCH_3$ | $N(CH_3)_2$ | |
| 0 | H | H | O | S | — | $CH_3$ | $CH_3$ | $CH_3$ | $CH(OCH_3)_2$ | |
| 0 | H | H | O | S | — | $CH_3$ | $CH_3$ | $OC_2H_5$ | $CH_3$ | |
| 0 | H | H | O | S | — | $CH_3$ | $CH_3$ | $OCH_3$ | $NHCH_3$ | |
| 0 | H | H | O | S | — | $CH_3$ | $CH_3$ | $CH_3$ | $SCH_3$ | |
| 0 | H | H | O | O | — | $CH_3$ | $CH_3$ | $CH_3$ | $-C\equiv CH$ | |
| 0 | H | H | O | S | — | $CH_3$ | $CH_3$ | $CH_3$ | $CHSCH_3$ | |
| 0 | H | H | O | S | — | $CH_3$ | $CH_3$ | $CH_3$ | $SCF_2H$ | |
| 0 | H | H | O | S | — | $CH_3$ | $CH_3$ | $OCH_3$ | $N(OCH_3)CH_3$ | |
| 0 | H | H | O | S | — | $CH_3$ | $CH_3$ | $CH_3$ | $OCH_2C\equiv CH$ | |

TABLE VII

J—SO₂NHC(O)N(R)—[pyrimidine with X₁, Y₁]

| J* | Q | W₁ | R₁ | R₃ | R₁₃ or R₁₅ | R₄ or R₁₄ or R₁₆ | X₁ | Y₁ | m.p. |
|---|---|---|---|---|---|---|---|---|---|
| 1 | 1 | S | H | — | | CH₃ | CH₃ | O | |
| 1 | 1 | O | H | — | | CH₃ | OCH₃ | O | |
| 1 | 1 | S | 5-Cl | — | | C₂H₅ | OCH₃ | CH₂ | |
| 1 | 1 | S | H | — | | CH₂CH=CH₂ | CH₃ | CH | |
| 1 | 1 | S | H | — | | C₆H₅ | OCH₃ | O | |
| 1 | 2 | — | H | — | CH₃ | CH₃ | OCH₃ | O | |
| 1 | 2 | — | H | — | | —(CH₂)₄— | OCH₃ | O | |
| 1 | 3 | S | H | — | CH₃ | CH₃ | OCH₃ | O | |
| 2 | 1 | S | — | — | | CH₃ | CH₃ | O | |
| 2 | 1 | S | — | — | | CH₃ | OCH₃ | O | |
| 2 | 1 | O | — | — | | CH₃ | OCH₃ | CH₂ | |
| 2 | 2 | — | — | — | CH₃ | CH₃ | OCH₃ | O | |
| 2 | 2 | — | — | — | | —(CH₂)₄— | OCH₃ | O | |
| 2 | 3 | S | — | — | CH₃ | CH₃ | OCH₃ | O | |
| 3 | 1 | S | — | — | | CH₃ | CH₃ | O | |
| 3 | 1 | S | — | — | | CH₃ | OCH₃ | O | |
| 3 | 1 | O | — | — | | CH₃ | OCH₃ | O | |
| 3 | 2 | — | — | — | CH₃ | CH₃ | OCH₃ | O | |
| 3 | 2 | — | — | — | | —(CH₂)₄— | OCH₃ | O | |
| 3 | 3 | S | — | — | CH₃ | CH₃ | OCH₃ | O | |
| 4 | 1 | S | — | — | | CH₃ | CH₃ | O | |
| 4 | 1 | S | — | — | | CH₃ | OCH₃ | O | |
| 4 | 1 | O | — | — | | CH₃ | OCH₃ | CH₂ | |
| 4 | 2 | — | — | — | CH₃ | CH₃ | OCH₃ | O | |
| 4 | 2 | — | — | — | | —(CH₂)₄— | OCH₃ | O | |
| 4 | 3 | S | — | — | CH₃ | CH₃ | OCH₃ | O | |
| 5 | 1 | S | — | H | | CH₃ | OCH₃ | O | |
| 5 | 1 | S | — | CH₃ | | CH₃ | OCH₃ | O | |
| 5 | 1 | O | — | H | | C₂H₅ | OCH₃ | CH₂ | |
| 5 | 2 | — | — | CH₃ | CH₃ | CH₃ | CH₃ | O | |
| 5 | 2 | — | — | H | | —(CH₂)₄— | OCH₃ | O | |
| 5 | 3 | S | — | CH₃ | CH₃ | CH₃ | OCH₃ | O | |
| 6 | 1 | S | — | H | | CH₃ | OCH₃ | O | |
| 6 | 1 | S | — | CH₃ | | CH₃ | OCH₃ | O | |
| 6 | 1 | O | — | H | | C₂H₅ | OCH₃ | CH₂ | |
| 6 | 2 | — | — | CH₃ | CH₃ | CH₃ | CH₃ | O | |
| 6 | 2 | — | — | H | | —(CH₂)₄— | OCH₃ | O | |
| 6 | 3 | S | — | CH₃ | CH₃ | CH₃ | OCH₃ | O | |
| 7 | 1 | S | — | H | | CH₃ | OCH₃ | O | |
| 7 | 1 | S | — | CH₃ | | CH₃ | OCH₃ | O | |
| 7 | 1 | O | — | H | | C₂H₅ | OCH₃ | CH₂ | |
| 7 | 2 | — | — | CH₃ | CH₃ | CH₃ | CH₃ | O | |
| 7 | 2 | — | — | H | | —(CH₂)₄— | OCH₃ | O | |
| 7 | 3 | S | — | CH₃ | CH₃ | CH₃ | OCH₃ | O | |
| 8 | 1 | S | — | H | | CH₃ | OCH₃ | O | |
| 8 | 1 | S | — | CH₃ | | CH₃ | OCH₃ | O | |
| 8 | 1 | O | — | H | | C₂H₅ | OCH₃ | CH₂ | |
| 8 | 2 | — | — | CH₃ | CH₃ | CH₃ | CH₃ | O | |
| 8 | 2 | — | — | H | | —(CH₂)₄— | OCH₃ | O | |
| 8 | 3 | S | — | CH₃ | CH₃ | CH₃ | OCH₃ | O | |

*where J is J-1, n = 0, R = H, E = single bond;
where J is J-2 to J-8, n = 0, R₂ = H, R = H.

TABLE VIII

J—SO₂NHC(O)N(R)—[pyrimidine with X₁, Y₁]

| J* | Q | W₁ | R₁ | R₃ | R₁₅ | R₄ or R₁₆ | X₁ | Y₁ | m.p. |
|---|---|---|---|---|---|---|---|---|---|
| 1 | 1 | S | H | — | | CH₃ | OCH₃ | CH₂ | |

TABLE VIII-continued

| J* | Q | W₁ | R₁ | R₃ | R₁₅ | R₄ or R₁₆ | X₁ | Y₁ | m.p. |
|---|---|---|---|---|---|---|---|---|---|
| 1 | 1 | O | H | — | | CH₃ | CH₃ | O | |

TABLE VIII-continued

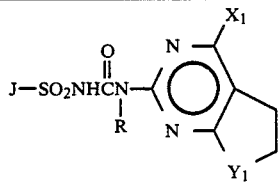

| J* | Q | W₁ | R₁ | R₃ | R₁₅ | R₁₆ | X₁ | Y₁ | m.p. |
|---|---|---|---|---|---|---|---|---|---|
| 1 | 1 | S | 5-Cl | — | | C₂H₅ | OCH₃ | O | |
| 1 | 1 | S | H | — | | CH₂CH=CH₂ | OCF₂H | O | |
| 1 | 1 | S | H | — | | C₆H₅ | OCH₃ | O | |
| 1 | 2 | — | H | — | CH₃ | CH₃ | OC₂H₅ | O | |
| 1 | 2 | — | H | — | —(CH₂)₄— | | OCH₃ | O | |
| 1 | 3 | S | H | — | CH₃ | CH₃ | OCH₃ | O | |
| 2 | 1 | S | — | — | | CH₃ | OCH₃ | O | |
| 2 | 1 | S | — | — | CH₃ | CH₃ | OCH₃ | O | |
| 2 | 1 | O | — | — | | CH₃ | OCH₃ | O | |
| 2 | 2 | — | — | — | CH₃ | CH₃ | OC₂H₅ | O | |
| 2 | 2 | — | — | — | —(CH₂)₄— | | OCH₃ | O | |
| 2 | 3 | S | — | — | CH₃ | CH₃ | OCH₃ | O | |
| 3 | 1 | S | — | — | | CH₃ | OCH₃ | O | |
| 3 | 1 | S | — | — | CH₃ | CH₃ | CH₃ | O | |
| 3 | 1 | O | — | — | | CH₃ | OCH₃ | O | |
| 3 | 2 | — | — | — | CH₃ | CH₃ | OC₂H₅ | O | |
| 3 | 2 | — | — | — | —(CH₂)₄— | | OCH₃ | O | |
| 3 | 3 | S | — | — | CH₃ | CH₃ | OCH₃ | O | |
| 4 | 1 | S | — | — | | CH₃ | OCH₃ | O | |
| 4 | 1 | S | — | — | CH₃ | CH₃ | | O | |
| 4 | 1 | O | — | — | | CH₃ | OCH₃ | O | |
| 4 | 2 | — | — | — | CH₃ | CH₃ | OC₂H₅ | O | |
| 4 | 2 | — | — | — | —(CH₂)₄— | | OCH₃ | O | |
| 4 | 3 | S | — | — | CH₃ | CH₃ | OCH₃ | O | |
| 5 | 1 | S | — | H | | CH₃ | OCH₃ | O | |
| 5 | 1 | S | — | CH₃ | CH₃ | CH₃ | CH₃ | O | |
| 5 | 1 | O | — | H | | C₂H₅ | OC₂H₅ | O | |
| 5 | 2 | — | — | — | CH₃ CH₃ | CH₃ | OCF₂H | O | |
| 5 | 2 | — | — | H | —(CH₂)₄— | | OCH₃ | O | |
| 5 | 3 | S | — | H | CH₃ | CH₃ | OCH₃ | O | |
| 6 | 1 | S | — | H | | CH₃ | OCH₃ | O | |
| 6 | 1 | S | — | CH₃ | CH₃ | CH₃ | CH₃ | O | |
| 6 | 1 | O | — | H | | C₂H₅ | OC₂H₅ | O | |
| 6 | 2 | — | — | — | CH₃ CH₃ | CH₃ | OCF₂H | O | |
| 6 | 2 | — | — | H | —(CH₂)₄— | | OCH₃ | O | |
| 6 | 3 | S | — | H | CH₃ | CH₃ | OCH₃ | O | |
| 7 | 1 | S | — | H | | CH₃ | OCH₃ | O | |
| 7 | 1 | S | — | CH₃ | CH₃ | CH₃ | CH₃ | O | |
| 7 | 1 | O | — | H | | C₂H₅ | OC₂H₅ | O | |
| 7 | 2 | — | — | — | CH₃ CH₃ | CH₃ | OCF₂H | O | |
| 7 | 2 | — | — | H | —(CH₂)₄— | | OCF₂H | O | |
| 7 | 3 | S | — | H | CH₃ | CH₃ | OCH₃ | O | |
| 8 | 1 | S | — | H | | CH₃ | OCH₃ | O | |
| 8 | 1 | S | — | CH₃ | CH₃ | CH₃ | CH₃ | O | |
| 8 | 1 | O | — | H | | C₂H₅ | OC₂H₅ | O | |
| 8 | 2 | — | — | — | CH₃ CH₃ | CH₃ | OCF₂H | O | |
| 8 | 2 | — | — | H | —(CH₂)₄— | | OCH₃ | O | |
| 8 | 3 | S | — | — | CH₃ | CH₃ | OCH₃ | O | |

*where J is J-1, n = 0, R = H, E = single bond;
where J is J-2 to J-8, n = 0, R₂ = H, R = H.

TABLE IX

J—SO₂NHCN structure with pyrimidine ring, X₁, Y₃ substituents

| J* | Q | W₁ | R₁ | R₃ | R₁₅ | R₁₆ | X₁ | Y₃ | m.p. |
|---|---|---|---|---|---|---|---|---|---|
| 1 | 1 | S | H | — | | CH₃ | OCH₃ | CH₃ | |
| 1 | 1 | O | H | — | | CH₃ | OCH₃ | CH₃ | |
| 1 | 1 | S | 5-Cl | — | | C₂H₅ | CH₃ | H | |

TABLE IX-continued

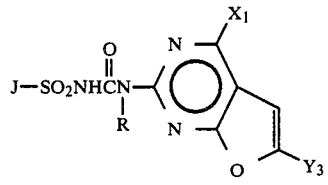

| J* | Q | W₁ | R₁ | R₃ | R₁₅ | R₁₆ | X₁ | Y₃ | m.p. |
|---|---|---|---|---|---|---|---|---|---|
| 1 | 1 | S | H | — | | CH₂CH=CH₂ | OCF₂H | CH₃ | |
| 1 | 1 | S | H | — | | C₆H₅ | OCH₃ | H | |
| 1 | 2 | — | H | — | CH₃ | CH₃ | OC₂H₅ | CH₃ | |
| 1 | 2 | — | H | — | —(CH₂)₄— | | OCH₃ | CH₃ | |
| 1 | 3 | S | H | — | CH₃ | CH₃ | OCH₃ | CH₃ | |
| 2 | 1 | S | — | — | | CH₃ | OCH₃ | CH₃ | |
| 2 | 1 | S | — | — | CH₃ | CH₃ | OCH₃ | H | |
| 2 | 1 | O | — | — | | CH₃ | OCH₃ | CH₃ | |
| 2 | 2 | — | — | — | CH₃ • CH₃ | | OC₂H₅ | CH₃ | |
| 2 | 2 | — | — | — | —(CH₂)₄— | | OCF₂H | H | |
| 2 | 3 | S | — | — | CH₃ | CH₃ | OCH₃ | CH₃ | |
| 3 | 1 | S | — | — | | CH₃ | OCH₃ | CH₃ | |
| 3 | 1 | S | — | — | CH₃ | CH₃ | OCH₃ | H | |
| 3 | 1 | O | — | — | | CH₃ | OCH₃ | CH₃ | |
| 3 | 2 | — | — | — | CH₃ | CH₃ | OC₂H₅ | CH₃ | |
| 3 | 2 | — | — | — | —(CH₂)₄— | | OCF₂H | H | |
| 3 | 3 | S | — | — | CH₃ | CH₃ | OCH₃ | CH₃ | |
| 4 | 1 | S | — | — | | CH₃ | OCH₃ | CH₃ | |
| 4 | 1 | S | — | — | CH₃ | CH₃ | OCH₃ | H | |
| 4 | 1 | O | — | — | | CH₃ | OCH₃ | CH₃ | |
| 4 | 2 | — | — | — | CH₃ | CH₃ | OC₂H₅ | CH₃ | |
| 4 | 2 | — | — | — | —(CH₂)₄— | | OCF₂H | H | |
| 4 | 3 | S | — | — | CH₃ | CH₃ | OCH₃ | CH₃ | |
| 5 | 1 | S | — | H | | CH₃ | OCH₃ | CH₃ | |
| 5 | 1 | S | — | CH₃ | CH₃ | CH₃ | CH₃ | H | |
| 5 | 1 | O | — | H | | C₂H₅ | OCH₃ | CH₃ | |
| 5 | 2 | — | — | — | CH₃ CH₃ | CH₃ | OCF₂H | H | |
| 5 | 2 | — | — | H | —(CH₂)₄— | | OCH₃ | CH₃ | |
| 5 | 3 | S | — | H | CH₃ | CH₃ | OCH₃ | CH₃ | |
| 6 | 1 | S | — | H | | CH₃ | OCH₃ | CH₃ | |
| 6 | 1 | S | — | CH₃ | CH₃ | CH₃ | CH₃ | H | |
| 6 | 1 | O | — | H | | C₂H₅ | OCH₃ | CH₃ | |
| 6 | 2 | — | — | — | CH₃ CH₃ | CH₃ | OCF₂H | H | |
| 6 | 2 | — | — | H | —(CH₂)₄— | | OCH₃ | CH₃ | |
| 6 | 3 | S | — | — | CH₃ CH₃ | CH₃ | OCH₃ | CH₃ | |
| 7 | 1 | S | — | H | | CH₃ | OCH₃ | CH₃ | |
| 7 | 1 | S | — | CH₃ | CH₃ | CH₃ | CH₃ | H | |
| 7 | 1 | O | — | H | | C₂H₅ | OCH₃ | CH₃ | |
| 7 | 2 | — | — | — | CH₃ CH₃ | CH₃ | OCF₂H | H | |
| 7 | 2 | — | — | H | —(CH₂)₄— | | OCH₃ | CH₃ | |
| 7 | 3 | S | — | — | CH₃ CH₃ | CH₃ | OCH₃ | CH₃ | |
| 8 | 1 | S | — | H | | CH₃ | OCH₃ | CH₃ | |
| 8 | 1 | S | — | CH₃ | CH₃ | CH₃ | CH₃ | H | |
| 8 | 1 | O | — | H | | C₂H₅ | OCH₃ | CH₃ | |
| 8 | 2 | — | — | — | CH₃ CH₃ | CH₃ | OCF₂H | H | |
| 8 | 2 | — | — | H | —(CH₂)₄— | | OCH₃ | CH₃ | |
| 8 | 3 | S | — | — | CH₃ CH₃ | CH₃ | OCH₃ | CH₃ | |

*where J is J-1, n = 0, R = H, E = single bond;
where J is J-2 to J-8, n = 0, R₂ = H, R = H.

TABLE X

J—SO₂NHCN structure with pyrazole-like ring, X₂, Y₂ substituents

| J* | Q | W₁ | R₁ | R₃ | R₁₅ | R₁₆ | X₂ | Y₂ | m.p. |
|---|---|---|---|---|---|---|---|---|---|
| 1 | 1 | S | H | — | | CH₃ | CH₃ | OCH₃ | |
| 1 | 1 | O | H | — | | CH₃ | CH₃ | OCH₃ | |
| 1 | 1 | S | 5-Cl | — | | C₂H₅ | C₂H₅ | OCF₂H | |
| 1 | 1 | S | H | — | | CH₂CH=CH₂ | CH₃ | SCH₃ | |
| 1 | 1 | S | H | — | | C₆H₅ | C₂H₅ | CH₃ | |
| 1 | 2 | — | H | — | CH₃ | CH₃ | CH₃ | SCF₂H | |
| 1 | 2 | — | H | — | —(CH₂)₄— | | CH₃ | OCH₃ | |

TABLE X-continued

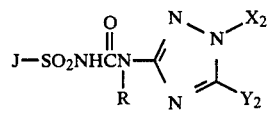

| J* | Q | W$_1$ | R$_1$ | R$_3$ | R$_{15}$ | R$_{16}$ | X$_2$ | R$_4$ or Y$_2$ | m.p. |
|---|---|---|---|---|---|---|---|---|---|
| 1 | 3 | S | H | — | CH$_3$ | CH$_3$ | CH$_3$ | OCH$_3$ | |
| 2 | 1 | S | — | — | | CH$_3$ | CH$_3$ | OCH$_3$ | |
| 2 | 1 | S | — | — | | CH$_3$ | C$_2$H$_5$ | OC$_2$H$_5$ | |
| 2 | 1 | O | — | — | | CH$_3$ | CH$_3$ | OCH$_3$ | |
| 2 | 2 | — | — | — | CH$_3$ | CH$_3$ | CH$_3$ | SCH$_3$ | |
| 2 | 2 | — | — | — | —(CH$_2$)$_4$— | | CH$_3$ | OC$_2$H$_5$ | |
| 2 | 3 | S | — | — | CH$_3$ | CH$_3$ | CH$_3$ | OCH$_3$ | |
| 3 | 1 | S | — | — | | CH$_3$ | CH$_3$ | OCH$_3$ | |
| 3 | 1 | S | — | — | | CH$_3$ | C$_2$H$_5$ | OC$_2$H$_5$ | |
| 3 | 1 | O | — | — | | CH$_3$ | CH$_3$ | OCH$_3$ | |
| 3 | 2 | — | — | — | CH$_3$ | CH$_3$ | CH$_3$ | SCH$_3$ | |
| 3 | 2 | — | — | — | —(CH$_2$)$_4$— | | CH$_3$ | OC$_2$H$_5$ | |
| 3 | 3 | S | — | — | CH$_3$ | CH$_3$ | CH$_3$ | OCH$_3$ | |
| 4 | 1 | S | — | — | | CH$_3$ | CH$_3$ | OCH$_3$ | |
| 4 | 1 | S | — | — | | CH$_3$ | C$_2$H$_5$ | OC$_2$H$_5$ | |
| 4 | 1 | O | — | — | | CH$_3$ | CH$_3$ | OCH$_3$ | |
| 4 | 2 | — | — | — | CH$_3$ | CH$_3$ | CH$_3$ | SCH$_3$ | |
| 4 | 2 | — | — | — | —(CH$_2$)$_4$— | | CH$_3$ | OC$_2$H$_5$ | |
| 4 | 3 | S | — | — | CH$_3$ | CH$_3$ | CH$_3$ | OCH$_3$ | |
| 5 | 1 | S | — | H | CH$_3$ | CH$_3$ | CH$_3$ | OCH$_3$ | |
| 5 | 1 | S | — | CH$_3$ | CH$_3$ | CH$_3$ | C$_2$H$_5$ | OCF$_2$H | |
| 5 | 1 | O | — | H | C$_2$H$_5$ | CH$_3$ | CH$_3$ | OCH$_3$ | |
| 5 | 2 | — | — | CH$_3$ | CH$_3$ | CH$_3$ | CH$_3$ | OC$_2$H$_5$ | |
| 5 | 2 | — | — | H | —(CH$_2$)$_4$— | | CH$_3$ | SCH$_3$ | |
| 5 | 3 | S | — | H | CH$_3$ | CH$_3$ | CH$_3$ | OCH$_3$ | |
| 6 | 1 | S | — | H | CH$_3$ | CH$_3$ | CH$_3$ | OCH$_3$ | |
| 6 | 1 | S | — | CH$_3$ | CH$_3$ | CH$_3$ | C$_2$H$_5$ | OCF$_2$H | |
| 6 | 1 | O | — | H | C$_2$H$_5$ | CH$_3$ | CH$_3$ | OCH$_3$ | |
| 6 | 2 | — | — | CH$_3$ | CH$_3$ | CH$_3$ | CH$_3$ | OC$_2$H$_5$ | |
| 6 | 2 | — | — | H | —(CH$_2$)$_4$— | | CH$_3$ | SCH$_3$ | |
| 6 | 3 | S | — | H | CH$_3$ | CH$_3$ | CH$_3$ | OCH$_3$ | |
| 7 | 1 | S | — | H | CH$_3$ | CH$_3$ | CH$_3$ | OCH$_3$ | |
| 7 | 1 | S | — | CH$_3$ | CH$_3$ | CH$_3$ | C$_2$H$_5$ | OCF$_2$H | |
| 7 | 1 | O | — | H | C$_2$H$_5$ | CH$_3$ | CH$_3$ | OCH$_3$ | |
| 7 | 2 | — | — | CH$_3$ | CH$_3$ | CH$_3$ | CH$_3$ | OC$_2$H$_5$ | |
| 7 | 2 | — | — | H | —(CH$_2$)$_4$— | | CH$_3$ | SCH$_3$ | |
| 7 | 3 | S | — | H | CH$_3$ | CH$_3$ | CH$_3$ | OCH$_3$ | |
| 8 | 1 | S | — | H | CH$_3$ | CH$_3$ | CH$_3$ | OCH$_3$ | |
| 8 | 1 | S | — | CH$_3$ | CH$_3$ | CH$_3$ | C$_2$H$_5$ | OCF$_2$H | |
| 8 | 1 | O | — | H | C$_2$H$_5$ | CH$_3$ | CH$_3$ | OCH$_3$ | |
| 8 | 2 | — | — | CH$_3$ | CH$_3$ | CH$_3$ | CH$_3$ | OC$_2$H$_5$ | |
| 8 | 2 | — | — | H | —(CH$_2$)$_4$— | | CH$_3$ | SCH$_3$ | |
| 8 | 3 | S | — | H | CH$_3$ | CH$_3$ | CH$_3$ | OCH$_3$ | |

*where J is J-1, n = 0, R = H, E = single bond;
where J is J-2 to J-8, n = 0, R$_2$ = H, R = H.

TABLE XI

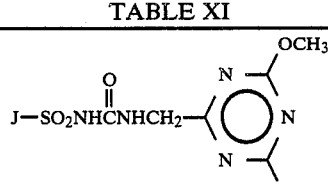

| J* | Q | W$_1$ | R$_1$ | R$_3$ | R$_{15}$ | R$_{16}$ | X$_3$ | m.p. |
|---|---|---|---|---|---|---|---|---|
| 1 | 1 | S | H | — | CH$_3$ | | OCH$_3$ | |
| 1 | 1 | O | H | — | CH$_3$ | | OCH$_3$ | |
| 1 | 1 | S | 5-Cl | — | C$_2$H$_5$ | | CH$_3$ | |
| 1 | 1 | S | H | — | CH$_2$CH=CH$_2$ | | OCH$_3$ | |
| 1 | 1 | S | H | — | C$_6$H$_5$ | | CH$_3$ | |
| 1 | 2 | — | H | — | CH$_3$ | CH$_3$ | CH$_3$ | |
| 1 | 2 | — | H | — | —(CH$_2$)$_4$— | | OCH$_3$ | |
| 1 | 3 | S | H | — | CH$_3$ | CH$_3$ | OCH$_3$ | |
| 2 | 1 | S | — | — | | CH$_3$ | CH$_3$ | |
| 2 | 1 | S | — | — | | CH$_3$ | OCH$_3$ | |
| 2 | 1 | O | — | — | | CH$_3$ | OCH$_3$ | |

TABLE XI-continued

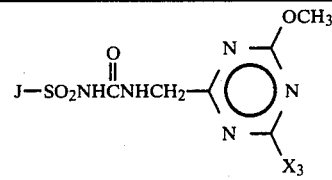

| J* | Q | W$_1$ | R$_1$ | R$_3$ | R$_{15}$ | R$_{16}$ | X$_3$ | m.p. |
|---|---|---|---|---|---|---|---|---|
| 2 | 2 | — | — | — | CH$_3$ | CH$_3$ | CH$_3$ | |
| 2 | 2 | — | — | — | —(CH$_2$)$_4$— | | OCH$_3$ | |
| 2 | 3 | S | — | — | CH$_3$ | CH$_3$ | OCH$_3$ | |
| 3 | 1 | S | — | — | | CH$_3$ | CH$_3$ | |
| 3 | 1 | S | — | — | | CH$_3$ | OCH$_3$ | |
| 3 | 1 | O | — | — | | CH$_3$ | OCH$_3$ | |
| 3 | 2 | — | — | — | CH$_3$ | CH$_3$ | CH$_3$ | |
| 3 | 2 | — | — | — | —(CH$_2$)$_4$— | | OCH$_3$ | |
| 3 | 3 | S | — | — | CH$_3$ | CH$_3$ | OCH$_3$ | |
| 4 | 1 | S | — | — | | CH$_3$ | CH$_3$ | |
| 4 | 1 | S | — | — | | CH$_3$ | OCH$_3$ | |
| 4 | 1 | O | — | — | | CH$_3$ | OCH$_3$ | |
| 4 | 2 | — | — | — | CH$_3$ | CH$_3$ | CH$_3$ | |
| 4 | 2 | — | — | — | —(CH$_2$)$_4$— | | OCH$_3$ | |
| 4 | 3 | S | — | — | CH$_3$ | CH$_3$ | OCH$_3$ | |
| 5 | 1 | S | — | H | CH$_3$ | | CH$_3$ | |
| 5 | 1 | S | — | CH$_3$ | CH$_3$ | | C$_2$H$_5$ | |
| 5 | 1 | O | — | H | C$_2$H$_5$ | | OCH$_3$ | |
| 5 | 2 | — | — | CH$_3$ | CH$_3$ | CH$_3$ | CH$_3$ | |
| 5 | 2 | — | — | H | —(CH$_2$)$_4$— | | OCH$_3$ | |
| 5 | 3 | S | — | H | CH$_3$ | CH$_3$ | OCH$_3$ | |
| 6 | 1 | S | — | H | CH$_3$ | | CH$_3$ | |
| 6 | 1 | S | — | CH$_3$ | CH$_3$ | | OCH$_3$ | |
| 6 | 1 | O | — | H | C$_2$H$_5$ | | OCH$_3$ | |
| 6 | 2 | — | — | CH$_3$ | CH$_3$ | CH$_3$ | CH$_3$ | |
| 6 | 2 | — | — | H | —(CH$_2$)$_4$— | | OCH$_3$ | |
| 6 | 3 | S | — | H | CH$_3$ | CH$_3$ | OCH$_3$ | |
| 7 | 1 | S | — | H | CH$_3$ | | CH$_3$ | |
| 7 | 1 | S | — | CH$_3$ | CH$_3$ | | OCH$_3$ | |
| 7 | 1 | O | — | H | C$_2$H$_5$ | | OCH$_3$ | |
| 7 | 2 | — | — | CH$_3$ | CH$_3$ | CH$_3$ | CH$_3$ | |
| 7 | 2 | — | — | H | —(CH$_2$)$_4$— | | OCH$_3$ | |
| 7 | 3 | S | — | CH$_3$ | CH$_3$ | CH$_3$ | OCH$_3$ | |
| 8 | 1 | S | — | H | CH$_3$ | | CH$_3$ | |
| 8 | 1 | S | — | CH$_3$ | CH$_3$ | | OCH$_3$ | |
| 8 | 1 | O | — | H | C$_2$H$_5$ | | OCH$_3$ | |
| 8 | 2 | — | — | CH$_3$ | CH$_3$ | CH$_3$ | CH$_3$ | |
| 8 | 2 | — | — | H | —(CH$_2$)$_4$— | | OCH$_3$ | |
| 8 | 3 | S | — | CH$_3$ | CH$_3$ | CH$_3$ | OCH$_3$ | |

*where J is J-1, n = 0, R = H, E = single bond;
where J is J-2 to J-8, n = 0, R$_2$ = H, R = H.

TABLE XII

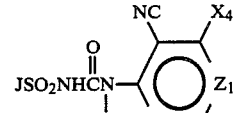

| J* | Q | W$_1$ | R$_1$ | R$_3$ | R$_{15}$ | R$_{16}$ | X$_4$ | Y$_4$ | Z$_1$ | m.p. |
|---|---|---|---|---|---|---|---|---|---|---|
| 1 | 1 | S | H | — | CH$_3$ | CH$_3$ | CH$_3$ | CH | | |
| 1 | 1 | O | H | — | CH$_3$ | OCH$_3$ | OCH$_3$ | CH | | |
| 1 | 1 | S | 5-Cl | — | C$_2$H$_5$ | CH$_3$ | CH$_3$ | N | | |
| 1 | 1 | S | H | — | CH$_2$CH=CH$_2$ | OCH$_3$ | CH$_3$ | CH | | |
| 1 | 1 | S | H | — | C$_6$H$_5$ | OCH$_3$ | OCH$_3$ | N | | |
| 1 | 2 | — | H | — | CH$_3$ | CH$_3$ | OCH$_3$ | Cl | CH | |
| 1 | 2 | — | H | — | —(CH$_2$)$_4$— | | OCH$_3$ | OCH$_3$ | CH | |
| 1 | 3 | S | H | — | CH$_3$ | CH$_3$ | OCH$_3$ | CH | | |
| 2 | 1 | S | — | — | | CH$_3$ | CH$_3$ | CH$_3$ | CH | |
| 2 | 1 | S | — | — | | CH$_3$ | OCH$_3$ | OCH$_3$ | N | |
| 2 | 1 | O | — | — | | CH$_3$ | OCH$_3$ | CH$_3$ | CH | |
| 2 | 2 | — | — | — | CH$_3$ | CH$_3$ | CH$_3$ | OCH$_3$ | CH | |

TABLE XII-continued $$\text{JSO}_2\text{NHCN}(R)-\text{[ring with NC, X}_4\text{, Z}_1\text{, Y}_4\text{, N]}$$

| J* | Q | W₁ | R₁ | R₃ | R₄ or R₁₅ | R₁₆ | X₄ | Y₄ | Z₁ | m.p. |
|---|---|---|---|---|---|---|---|---|---|---|
| 2 | 2 | — | — | — | —(CH₂)₄— | | OCH₃ | Cl | CH | |
| 2 | 3 | S | — | — | CH₃ | CH₃ | OCH₃ | OCH₃ | CH | |
| 3 | 1 | S | — | — | CH₃ | | CH₃ | CH₃ | CH | |
| 3 | 1 | S | — | — | CH₃ | | OCH₃ | OCH₃ | N | |
| 3 | 1 | O | — | — | CH₃ | | OCH₃ | CH₃ | CH | |
| 3 | 2 | — | — | — | CH₃ | CH₃ | CH₃ | OCH₃ | CH | |
| 3 | 2 | — | — | — | —(CH₂)₄— | | CH₃ | Cl | CH | |
| 3 | 3 | S | — | — | CH₃ | CH₃ | OCH₃ | OCH₃ | CH | |
| 4 | 1 | S | — | — | CH₃ | | CH₃ | CH₃ | CH | |
| 4 | 1 | S | — | — | CH₃ | | OCH₃ | OCH₃ | N | |
| 4 | 1 | O | — | — | CH₃ | | OCH₃ | CH₃ | CH | |
| 4 | 2 | — | — | — | CH₃ | CH₃ | CH₃ | OCH₃ | CH | |
| 4 | 2 | — | — | — | —(CH₂)₄— | | OCH₃ | Cl | CH | |
| 4 | 3 | S | — | — | CH₃ | CH₃ | OCH₃ | OCH₃ | CH | |
| 5 | 1 | S | — | H | CH₃ | | CH₃ | CH₃ | CH | |
| 5 | 1 | S | — | CH₃ | CH₃ | | OCH₃ | OCH₃ | N | |
| 5 | 1 | O | — | H | C₂H₅ | | CH₃ | OCH₃ | CH | |
| 5 | 2 | — | — | CH₃ | CH₃ | CH₃ | OCH₃ | CH₃ | CH | |
| 5 | 2 | — | — | H | —(CH₂)₄— | | OCH₃ | Cl | CH | |
| 5 | 3 | S | — | CH₃ | CH₃ | CH₃ | OCH₃ | OCH₃ | CH | |
| 6 | 1 | S | — | H | CH₃ | | CH₃ | CH₃ | CH | |
| 6 | 1 | S | — | CH₃ | CH₃ | | OCH₃ | OCH₃ | N | |
| 6 | 1 | O | — | H | C₂H₅ | | CH₃ | OCH₃ | CH | |
| 6 | 2 | — | — | CH₃ | CH₃ | CH₃ | OCH₃ | CH₃ | CH | |
| 6 | 2 | — | — | H | —(CH₂)₄— | | OCH₃ | Cl | CH | |
| 6 | 3 | S | — | CH₃ | CH₃ | CH₃ | OCH₃ | OCH₃ | CH | |
| 7 | 1 | S | — | H | CH₃ | | CH₃ | CH₃ | CH | |
| 7 | 1 | S | — | CH₃ | CH₃ | | OCH₃ | OCH₃ | N | |
| 7 | 1 | O | — | H | C₂H₅ | | CH₃ | OCH₃ | CH | |
| 7 | 2 | — | — | CH₃ | CH₃ | CH₃ | OCH₃ | CH₃ | CH | |
| 7 | 2 | — | — | H | —(CH₂)₄— | | OCH₃ | Cl | CH | |
| 7 | 3 | S | — | CH₃ | CH₃ | CH₃ | OCH₃ | OCH₃ | CH | |
| 8 | 1 | S | — | H | CH₃ | | CH₃ | CH₃ | CH | |
| 8 | 1 | S | — | CH₃ | CH₃ | | OCH₃ | OCH₃ | N | |
| 8 | 1 | O | — | H | C₂H₅ | | CH₃ | OCH₃ | CH | |
| 8 | 2 | — | — | CH₃ | CH₃ | CH₃ | OCH₃ | CH₃ | CH | |
| 8 | 2 | — | — | H | —(CH₂)₄— | | OCH₃ | Cl | CH | |
| 8 | 3 | S | — | CH₃ | CH₃ | CH₃ | OCH₃ | OCH₃ | CH | |

*where J is J-1, n = 0, R = H, E = single bond;
where J is J-2 to J-8, n = 0, R₂ = H, R = H.

TABLE XIII $$\text{J—SO}_2\text{NHCN}(R)-\text{[ring with X, Z, Y, N]}$$

| J* | Q | W₁ | R₃ | R₄ or R₁₅ | R₁₆ | X | Y | Z | m.p.(°C.) |
|---|---|---|---|---|---|---|---|---|---|
| 2 | 1 | S | — | CH₃ | | CH₃ | CH₃ | CH | |
| 2 | 1 | S | — | CH₃ | | CH₃ | CH₃ | CH | |
| 2 | 1 | S | — | CH₃ | | OCH₃ | OCH₃ | CH | |
| 2 | 1 | S | — | CH₃ | | OCH₃ | Cl | CH | |
| 2 | 1 | S | — | CH₃ | | OCH₃ | CH₃ | N | |
| 2 | 1 | S | — | CH₃ | | OCH₃ | OCH₃ | N | |
| 2 | 1 | O | — | CH₃ | | OCH₃ | CH₃ | CH | |
| 2 | 1 | O | — | CH₃ | | OCH₃ | OCH₃ | CH | |
| 2 | 1 | O | — | CH₃ | | CH₃ | CH₃ | N | |
| 2 | 2 | — | — | CH₃ | CH₃ | CH₃ | OCH₃ | CH | |
| 2 | 2 | — | — | CH₃ | CH₃ | OCH₃ | OCH₃ | CH | |
| 2 | 2 | — | — | CH₃ | CH₃ | OCH₃ | CH₃ | N | |
| 2 | 2 | — | — | CH₃ | CH₃ | OCH₃ | OCH₃ | N | |

TABLE XIII-continued $$\text{J—SO}_2\text{NHCN}(R)-\text{[ring with X, Z, Y, N]}$$

| J* | Q | W₁ | R₃ | R₄ or R₁₅ | R₁₆ | X | Y | Z | m.p.(°C.) |
|---|---|---|---|---|---|---|---|---|---|
| 2 | 2 | — | — | —(CH₂)₄— | | CH₃ | OCH₃ | CH | |
| 2 | 2 | — | — | —(CH₂)₄— | | OCH₃ | OCH₃ | CH | |
| 2 | 2 | — | — | —(CH₂)₄— | | CH₃ | OCH₃ | N | |
| 2 | 2 | — | — | —(CH₂)₄— | | OCH₃ | OCH₃ | N | |
| 2 | 3 | S | — | CH₃ | CH₃ | OCH₃ | OCH₃ | CH | |
| 3 | 1 | S | — | CH₃ | | CH₃ | CH₃ | CH | |
| 3 | 1 | S | — | CH₃ | | CH₃ | OCH₃ | CH | |
| 3 | 1 | S | — | CH₃ | | OCH₃ | OCH₃ | CH | |
| 3 | 1 | S | — | CH₃ | | OCH₃ | Cl | CH | |
| 3 | 1 | S | — | CH₃ | | OCH₃ | CH₃ | N | |
| 3 | 1 | S | — | CH₃ | | OCH₃ | OCH₃ | N | |
| 3 | 1 | O | — | CH₃ | | OCH₃ | CH₃ | CH | |
| 3 | 1 | O | — | CH₃ | | OCH₃ | OCH₃ | CH | |
| 3 | 1 | O | — | CH₃ | | CH₃ | OCH₃ | N | |
| 3 | 2 | S | — | CH₃ | CH₃ | CH₃ | OCH₃ | CH | 187–188 |
| 3 | 2 | S | — | CH₃ | CH₃ | OCH₃ | OCH₃ | CH | 193–194 |
| 3 | 2 | S | — | CH₃ | CH₃ | OCH₃ | CH₃ | N | |
| 3 | 2 | S | — | CH₃ | CH₃ | OCH₃ | OCH₃ | N | 182–183 |
| 3 | 2 | S | — | CH₃ | CH₃ | Cl | OCH₃ | CH | 183–185 |
| 3 | 2 | S | — | —(CH₂)₄— | | CH₃ | OCH₃ | CH | |
| 3 | 2 | S | — | —(CH₂)₄— | | OCH₃ | OCH₃ | CH | |
| 3 | 2 | S | — | —(CH₂)₄— | | OCH₃ | CH₃ | N | |
| 3 | 2 | S | — | —(CH₂)₄— | | OCH₃ | OCH₃ | N | |
| 3 | 3 | S | — | CH₃ CH₃ | | OCH₃ | OCH₃ | CH | |
| 4 | 1 | S | — | CH₃ | | CH₃ | CH₃ | CH | |
| 4 | 1 | S | — | CH₃ | | OCH₃ | OCH₃ | CH | |
| 4 | 1 | S | — | CH₃ | | CH₃ | OCH₃ | N | |
| 4 | 1 | O | — | CH₃ | | OCH₃ | OCH₃ | CH | |
| 4 | 2 | — | — | CH₃ | CH₃ | OCH₃ | OCH₃ | CH | |
| 4 | 2 | — | — | —(CH₂)₄— | | OCH₃ | OCH₃ | CH | |
| 4 | 3 | S | — | CH₃ | CH₃ | OCH₃ | OCH₃ | CH | |
| 5 | 1 | S | H | CH₃ | | CH₃ | OCH₃ | CH | |
| 5 | 1 | S | CH₃ | CH₃ | | OCH₃ | OCH₃ | CH | |
| 5 | 1 | S | H | CH₃ | | CH₃ | CH₃ | N | |
| 5 | 1 | O | H | CH₃ | | OCH₃ | OCH₃ | CH | |
| 5 | 2 | — | H | CH₃ | CH₃ | OCH₃ | OCH₃ | CH | |
| 5 | 2 | — | H | —(CH₂)₄— | | OCH₃ | OCH₃ | CH | |
| 5 | 3 | S | H | CH₃ | CH₃ | OCH₃ | OCH₃ | CH | |
| 6 | 1 | S | H | CH₃ | | CH₃ | OCH₃ | CH | |
| 6 | 1 | S | CH₃ | CH₃ | | OCH₃ | OCH₃ | CH | |
| 6 | 1 | S | H | CH₃ | | CH₃ | OCH₃ | N | |
| 6 | 1 | O | H | CH₃ | | OCH₃ | OCH₃ | CH | |
| 6 | 2 | — | H | CH₃ | CH₃ | OCH₃ | OCH₃ | CH | |
| 6 | 2 | — | H | —(CH₂)₄— | | OCH₃ | OCH₃ | CH | |
| 6 | 3 | S | H | CH₃ | CH₃ | OCH₃ | OCH₃ | CH | |
| 7 | 1 | S | H | CH₃ | | CH₃ | OCH₃ | CH | |
| 7 | 1 | S | CH₃ | CH₃ | | OCH₃ | OCH₃ | CH | |
| 7 | 1 | S | H | CH₃ | | CH₃ | OCH₃ | N | |
| 7 | 1 | O | H | CH₃ | | OCH₃ | OCH₃ | CH | |
| 7 | 2 | — | H | CH₃ | CH₃ | OCH₃ | OCH₃ | CH | |
| 7 | 2 | — | H | —(CH₂)₄— | | OCH₃ | OCH₃ | CH | |
| 7 | 3 | S | H | CH₃ | CH₃ | OCH₃ | OCH₃ | N | |
| 8 | 1 | S | H | CH₃ | | CH₃ | OCH₃ | CH | |
| 8 | 1 | S | CH₃ | CH₃ | | OCH₃ | OCH₃ | CH | |
| 8 | 1 | S | H | CH₃ | | CH₃ | OCH₃ | N | |
| 8 | 1 | O | H | CH₃ | | OCH₃ | OCH₃ | CH | |
| 8 | 2 | — | H | CH₃ | CH₃ | OCH₃ | OCH₃ | CH | |
| 8 | 2 | — | H | —(CH₂)₄— | | OCH₃ | OCH₃ | CH | |
| 8 | 3 | S | H | CH₃ | CH₃ | OCH₃ | OCH₃ | CH | |

*n = 0, R = H, R₂ = H.

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 5% to 99.9% solid or liquid diluent(s). More specifically. they will contain these ingredients in the following approximate proportions:

|  | Active Ingredient | Weight Percent | |
|---|---|---|---|
|  |  | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are somtimes desirable, and are achieved by incorporation into the formulation or by tank mixing.

Typical solid diluents are described in Watkins, et al.. "Handbook of Insecticide Dust Diluents and Carriers". 2nd Ed.. Dorland Books, Caldwell, New Jersey. The more absorptive diluents are preferred for wettable powders and the denser ones for dusts. Typical liquid diluents and solvents are described in Marsden, "Solvents Guide," 2nd Ed.. Interscience, New York. 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J. as well as Sisely and Wood. "Encyclopedia of surface Active Agents", Chemical Publishing Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet millinq (see, for example, Littler, U.S. Pat. No. 3,060,084). Granules and pellets may be made by spraying the active material upon preformed granular carriers by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, N.Y. 1963, pp. 8-14 59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

EXAMPLE 6

High Strength Concentrate

2-[[(4,6-dimethoxypyrimidin-2-yl)aminocarbonyl]aminosulfonyl]-N,N-dimethylbenzenecarbothioamide: 98.5% silica aerogel: 0.5% synthetic amorphous fine silica: 1.0%

The ingredients are blended and ground in a hammermill to produce a high strength concentrate essentially all passing a U.S.S. No. 50 screen (0.3 mm opening). This material may then be formulated in a variety of ways.

EXAMPLE 7

Wettable Powder

N-[(4,6-dimethoxypyrimidin-2-yl)aminocarbonyl]-2-(1-pyrrolidinylthioxomethyl)benzenesulfonamide: 40% dioctyl sodium sulfosuccinate: 1.5% sodium ligninsulfonate: 3% low viscosity methyl cellulose: 1.5% attapulgite: 54%

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 8

Oil Suspension

2-[[(4,6-dimethoxypyrimidin-2-yl)aminocarbonyl]aminosulfonyl]-N,N-dimethylbenzenecarbothioamide: 35% blend of polyalcohol carboxylic esters 6% and oil-soluble petroleum sulfonates:

xylene: 59%

The ingredients are combined and ground together in a sand mill to produce particles essentially all below 3 microns. The product can be used directly, extended with oils, or emulsified in water.

EXAMPLE 9

Extruded Pellet

N-[(4,6-dimethoxypyrimidin-2-yl)aminocarbonyl]-2-(1-pyrrolidinylthioxomethyl)benzenesulfonamide: 25% anhydrous sodium sulfate: 10% crude calcium ligninsulfonate: 5% sodium alkylnaphthalenesulfonate: 1% calcium/magnesium bentonite: 59%

The ingredients are blended, hammermilled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

High Strength Concentrate

2-[[(4,6-dimethoxypyrimidin-2-yl)aminocarbonyl-]aminosulfonyl]-N,N-dimethylbenzenecarbothioamide; 99% trimethylnonyl polyethylene glycol ether: 1%

The surfactant is sprayed upon the active ingredient in a blender and the mixture sifted through a U.S.S. No. 40 sieve (0.42 mm openings) prior to packaging. The concentrate may be formulated further for practical use.

EXAMPLE 11

Granule

N-[(4,6-dimethoxypyrimidin-2-yl)aminocarbonyl]-2-(1-pyrrolidinylthioxomethyl)benzenesulfonamide: 10%
attapulgite granules (low volative 90% matter, 0.71/0.30 mm; U.S.S. No. 25–50 sieves):

The active ingredient is warmed to approximately 100° C. and sprayed upon dedusted and pre-warmed attapulgite granules in a double-cone blender. The granules are then allowed to cool and are packaged.

EXAMPLE 12

Wettable Powder

2-[[(4,6-dimethoxypyrimidin-2-yl)aminocarbonyl-]aminosulfonyl]-N,N-dimethylbenzenecarbothioamide: 50%
sodium alkylnaphthalenesulfonate: 2%
low viscosity methyl cellulose: 2%
diatomaceous earth: 46%.

The ingredients are blended, coarsely hammermilled and then air milled to produce particles of active essentially all below 10 microns in diameter. The product is reblended before packaging.

EXAMPLE 13

Wettable Powder

N-[(4,6-dimethoxypyrimidin-2-yl)aminocarbonyl]-2-(1-pyrrolidinylthioxomethyl)benzenesulfonamide: 80%
sodium alkylnaphthalenesulfonate: 2%
sodium ligninsulfonate: 2%
synthetic amorphous silica: 3%
kaolinite: 13%

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 14

Granule wettable powder of Example 13: 15%
gypsum: 69%
potassium sulfate: 16%

The ingredients are blended in a rotating mixer and water sprayed on to accomplish granulation. When most of the material has reached the desired range of 1.0 to 0.42 mm (U.S.S. No. 18–40 sieves), the granules are removed, dried, and screened, oversize material is crushed to produce additional material in the desired range. These granules contain 12% active ingredient.

EXAMPLE 15

Oil Suspension

2-[[(4,6-dimethoxypyrimidin-2-yl)aminocarbonyl-]aminosulfonyl]-N,N-dimethylbenzenecarbothioamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 16

Aqueous Suspension

N-[(4,6-dimethoxypyrimidin-2-yl)aminocarbonyl]-2-(1-pyrrolidinylthioxomethyl)benzenesulfonamide: 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to diameters under 10 microns.

EXAMPLE 17

Wettable Powder

2-[[(4,6-dimethoxypyrimidin-2-yl)aminocarbonyl-]aminosulfonyl]-N,N-dimethylbenzenecarbothioamide: 65%
dodecylphenol polyethylene glycol ether: 2%
sodium ligninsulfonate: 4%
sodium silicoaluminate: 6%
montmorillonite (calcined): 23%

The ingredients are thoroughly blended. The liguid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide diphenylether, carbamate, and bipyridylium types.

The herbicidal properties of the subject compounds were discovered in a number of greenhouse tests. The test procedures and results follow.

Test A

Seeds of crabgrass (Digitaria sp.), giant foxtail (Setaria faberi), barnyardgrass (Echinochloa crusgalli), wild oats (Avena fatua), cheatgrass (Bromus secalinus), velvetleaf (Abutilon theophrasti), morningglory (Ipomoea spp.), cocklebur (Xanthium pennsylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to &=complete kill. The accompanying descriptive symbols have the following meanings:

C=chlorosis or necrosis
B=burn
D=defoliation
E=emergence inhibition
G=growth retardation
H=formative effects
U=unusual pigmentation
X=axillary stimulation
S=albinism
6Y=abscised buds or flowers.

Compounds

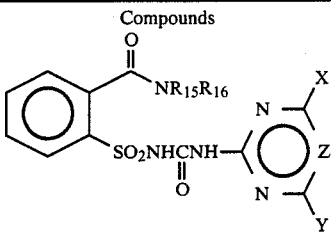

| Compound | $R_{15}$ | $R_{16}$ | X | Y | Z |
|---|---|---|---|---|---|
| 1 | $-CH_2CH_2CH_2CH_2-$ | | $OCH_3$ | $OCH_3$ | CH |
| 2 | $-CH_2CH_2CH_2CH_2-$ | | $OCH_3$ | $OCH_3$ | N |
| 3 | $CH_3$ | $CH_3$ | $OCH_3$ | $OCH_3$ | CH |
| 4 | $CH_3$ | H | $CH_3$ | $CH_3$ | CH |
| 5 | $CH_3$ | H | $CH_3$ | $OCH_3$ | CH |
| 6 | $CH_3$ | H | $OCH_3$ | $OCH_3$ | CH |
| 7 | $CH_3$ | H | Cl | $OCH_3$ | CH |
| 8 | $CH_2CH_3$ | H | $CH_3$ | $CH_3$ | CH |
| 9 | $CH_2CH_3$ | H | $CH_3$ | $OCH_3$ | CH |
| 10 | $CH_2CH_3$ | H | $OCH_3$ | $OCH_3$ | CH |
| 11 | $CH_2CH_3$ | H | Cl | $OCH_3$ | CH |
| 12 | $CH_2CH_3$ | H | $CH_3$ | $OCH_3$ | N |

Compound 13

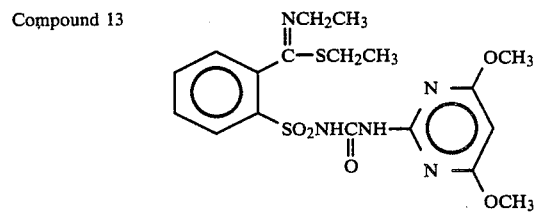

TABLE A

| | Cmpd. 1 | Cmpd. 2 | Compound 3 | | Compound 4 | | Compound 5 | | Compound 6 | | Compound 7 | |
|---|---|---|---|---|---|---|---|---|---|---|---|---|
| Rate kg/ha | 0.05 | 0.05 | 0.05 | 0.01 | 0.05 | 0.01 | 0.05 | 0.01 | 0.05 | 0.01 | 0.05 | 0.01 |
| | | | | | POSTEMERGENCE | | | | | | | |
| Morningglory | 10C | 4C,9G | 10C | 2C,8G | 4C,8H | 5H | 5C,9G | 3C,8H | 9C | 4C,8H | 6C,9G | 2C,5H |
| Cocklebur | 9C | 4C,9G | 5C,9G | 2C,7G | 4C,9H | 2C,7H | 4C,9H | 2C,6H | 9H | 5G | 3C,9H | 4H |
| Velvetleaf | 9C | 4C,5H | 9C | 4C,9H | 3C,7H | 1C | 4C,9H | 3C,4G | 9C | 4C,8H | 3C,4G | 1C |
| Nutsedge | 9G | 3G | 6C,9G | 3C,9G | 2C | 0 | 3C,8G | 0 | 3C,9G | 0 | 3G | 0 |
| Crabgrass | 4G | 0 | 3C,9G | 4G | 5G | 0 | 4G | 0 | 1C,3G | 0 | 0 | 0 |
| Giant Foxtail | — | — | — | — | 3C,8H | 2G | 3C,8G | 4G | 4C,8H | 3C,7H | 2C,5G | 2G |
| Barnyardgrass | 5C,9H | 9H | 9C | 9C | 5C,9H | 3H | 4C,9H | 3C,7H | 9C | 6C,9H | 3C,9H | 7H |
| Cheatgrass | 8G | 3G | 3C,9G | 2C,8G | 4C,9G | 4G | 4C,9G | 3C,7G | 4C,8G | 3C,8G | 6G | 0 |
| Wild Oats | 4C,8G | 0 | 5C,9G | 3C,9G | 3C,7G | 1C | 2C | 0 | 3G | 0 | 0 | 0 |
| Wheat | 9C | 0 | 4C,9G | 3C,9G | 5G | 0 | 2G | 0 | 5G | 0 | 0 | 0 |
| Corn | 3U,9G | 2U,9G | 3C,9H | 3C,8H | 1C,5H | 0 | 2C,6G | 0 | 2C,5G | 0 | 0 | 0 |
| Barley | — | — | — | — | 2C,6G | 0 | 4G | 0 | 7G | 0 | 0 | 0 |
| Soybean | 4C,9G | 3C,9G | 4C,9G | 4C,9H | 3C,7H | 3C,3H | 3C,9G | 3C,7G | 6C,9G | 4C,8G | 3C,5H | 2C,2H |
| Rice | 5C,9G | 2C,8G | 9C | 5C,9G | 5C,9G | 3C,7G | 9C | 3C,7G | 6C,9G | 5C,9G | 6G | 3C,7G |
| Sorghum | 3C,9H | 3C,8G | 9C | 2C,9H | 4C,9G | 2C,5G | 3C,9H | 3C,5G | 5C,9G | 4C,9H | 4C,9H | 3C,7H |
| Sugar beet | 5C,9G | 3C,8H | 9C | 5C,9G | 9C | 4C,9G | 9C | 4C,9G | 9C | 9C | 3C,7H | 6H |
| Cotton | 4C,9G | 4C,8H | 9C | 5C,9G | 9C | 0 | 10C | 10C | 10C | 10C | 10C | 3C,7G |
| | | | | | PREEMERGENCE | | | | | | | |
| Morningglory | 5H | 0 | 9G | 8G | 0 | 0 | 1C | 0 | 7H | 0 | 0 | 0 |
| Cocklebur | 2G | 0 | 8H | 6G | 0 | 0 | 2G | — | — | 0 | 0 | 0 |
| Velvetleaf | 5G | 0 | 5C,9G | 2C,8G | 0 | 0 | 8G | 3G | 6G | 4G | 0 | 0 |
| Nutsedge | 4C,8G | 0 | 10E | 3G | 0 | 0 | 3G | 0 | 5G | 0 | 0 | 0 |
| Crabgrass | 2C | 0 | 4G | 0 | 0 | 0 | — | 0 | 0 | 0 | 0 | 0 |
| Giant Foxtail | — | — | — | — | 0 | 0 | 0 | 0 | 9H | 0 | 0 | 0 |
| Barnyardgrass | 3C,7H | 0 | 3C,9H | 3C,7H | 0 | 0 | 0 | 0 | 9H | 3G | 0 | 0 |
| Cheatgrass | 2C,6G | 0 | 3C,9G | 6G | 0 | 0 | 0 | 0 | 7G | 2G | 0 | 0 |
| Wild Oats | 2C,6G | 0 | 5C,9G | 3C,6G | 0 | 0 | 0 | 0 | 1C | 0 | 0 | 0 |
| Wheat | 3C,7G | 0 | 3C,9G | 2C,6G | 0 | 0 | 3G | 0 | 2G | 0 | 0 | 0 |
| Corn | 4G | 0 | 9G | 2C,3G | 0 | 0 | 0 | 0 | 3G | 0 | 0 | 0 |
| Barley | — | — | — | — | 0 | 0 | 0 | 0 | 2G | 0 | 0 | 0 |
| Soybean | 0 | 0 | 6G | 6H | 1C | 0 | 1H | 0 | 1C | 0 | 0 | 0 |

TABLE A-continued

|  | | | | | | | | | | | | |
|---|---|---|---|---|---|---|---|---|---|---|---|---|
| Rice | 6G | 0 | 10E | 8H | 0 | 0 | 8G | 0 | 9H | 3C,8G | 0 | 0 |
| Sorghum | 2C,3H | 0 | 9H | 4C,8G | 0 | 0 | 0 | 0 | 4C,8H | 3C,6G | 0 | 0 |
| Sugar beet | 9G | 0 | 4C,9G | 4C,9G | 0 | 0 | 3G | 2H | 3C,6G | 3H | 0 | 0 |
| Cotton | 0 | 0 | 9G | 8G | 0 | 0 | 0 | 0 | 5G | 0 | 0 | 0 |

| | Compound 8 | | Compound 9 | | Compound 10 | | Compound 11 | | Compound 12 | | Compound 13 | |
|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | |
| Morningglory | 3C,8H | 3C,7H | 10C | 4C,8G | 4C,9G | 2C,7G | 2C,8G | 3C,6G | 3C,8G | 2C,4H | 2C,4G | 0 |
| Cocklebur | 3C,9H | 3C,6G | 5C,9H | 4C,9H | 3C,9H | 3G | 3C,9G | 2C,2H | 3C,9H | 2C,7G | 2C,4G | 0 |
| Velvetleaf | 3C,8H | 3C,8G | 9C | 4C,8H | 9C | 4C,9G | 2C,8G | 2C,8G | 3C,7H | 2G | 1C | 0 |
| Nutsedge | 3G | 0 | 3C,9G | 3G | 7G | 2G | 2G | 0 | 0 | 0 | 5G | 0 |
| Crabgrass | 0 | 0 | 4G | 3G | 4G | 3G | 2G | 0 | 0 | 0 | 2G | 0 |
| Giant Foxtail | 3G | 2G | 3C,7G | 3G | 2C,8G | 4G | 3G | 0 | 2G | 0 | 4G | 2G |
| Barnyardgrass | 2C,5G | 2H | 9C | 2C,5H | 9C | 3C,7H | 2C,6H | 3H | 4H | 0 | 3C,9H | 2C,8H |
| Cheatgrass | 8G | 0 | 9C | 5C,9G | 6G | 0 | 0 | 0 | 0 | 0 | 9G | 5G |
| Wild Oats | 1C | 0 | 2C,2G | 0 | 0 | 0 | 0 | 0 | 0 | 0 | 1C | 0 |
| Wheat | 0 | 0 | 2G | 0 | 0 | 0 | 0 | 0 | 0 | 0 | 2G | 0 |
| Corn | 1H | 1H | 2G | 0 | 3C,6G | 0 | 0 | 0 | 2C,5G | 0 | 2G | 0 |
| Barley | 0 | 0 | 2G | 0 | 1C | 0 | 0 | 0 | 0 | 0 | 3G | 0 |
| Soybean | 3C,7H | 0 | 4C,9G | 3C,8H | 4C,9H | 2C,8H | 4G | 2G | 2C,7G | 3C,4H | 3C,7H | 2C,2H |
| Rice | 0 | 0 | 2C,6G | 0 | 5C,9G | 2C,8G | 0 | 0 | 0 | 0 | 0 | 0 |
| Sorghum | 2C,5G | 2G | 2C,7G | 0 | 9H | 7G | 2C,8G | 2G | 5G | 0 | 3C,8H | 2C |
| Sugar beet | 3C,8G | 2C,7G | 9C | 9C | 9C | 4C,8G | 3C,7G | 3G | 9C | 3C,7G | 3C,8H | 2C,5H |
| Cotton | 3C,5G | 2G | 10C | 7G | 9C | 3C,8G | 9G | 2G | 7G | 5G | 3C,8G | 1C |
| PREEMERGENCE | | | | | | | | | | | | |
| Morningglory | 3G | 0 | 3H | 2H | 6G | 0 | 4G | 0 | 3G | 0 | 0 | 0 |
| Cocklebur | 0 | 4G | 2H | 0 | 6G | 0 | 0 | 0 | — | 0 | 0 | 0 |
| Velvetleaf | — | — | — | — | — | 0 | 8G | — | 0 | 0 | 0 | 0 |
| Nutsedge | 0 | 0 | 0 | 0 | 0 | 0 | 0 | 0 | 0 | 0 | 0 | 0 |
| Crabgrass | 3G | 0 | 0 | 0 | 3G | 0 | 4G | 2G | 3G | 0 | 0 | 0 |
| Giant Foxtail | 3G | 0 | 0 | 0 | 4G | 2G | 4G | 2G | 2G | 0 | 0 | 0 |
| Barnyardgrass | 2G | 0 | 0 | 0 | 5G | 4G | 5G | 5G | 0 | 0 | 0 | 0 |
| Cheatgrass | 5G | 0 | 0 | 0 | 5G | 0 | 0 | 0 | 0 | 0 | 0 | 0 |
| Wild Oats | 0 | 0 | 0 | 0 | 0 | 0 | 0 | 0 | 0 | 0 | 0 | 0 |
| Wheat | 0 | 0 | 0 | 0 | 2G | 0 | 0 | 0 | 0 | 0 | 0 | 0 |
| Corn | 0 | 0 | 2G | 0 | 4G | 0 | 2G | 0 | 2G | 0 | 2G | 0 |
| Barley | 0 | 0 | 0 | 0 | 0 | 0 | 3G | 0 | 2G | 0 | 0 | 0 |
| Soybean | 4G | 3G | 2C | 0 | 3G | 2G | 3G | 0 | 7G | 0 | 0 | 0 |
| Rice | 0 | 0 | 0 | 0 | 5G | 3G | 0 | 0 | 0 | 0 | 0 | 0 |
| Sorghum | 2G | 0 | 2C | 0 | 4G | 2G | 4G | 0 | 0 | 0 | 0 | 0 |
| Sugar beet | 3G | 0 | 2C,5G | 0 | 7G | 5G | 5G | 3G | 9G | 0 | 0 | 0 |
| Cotton | 3G | 0 | 9G | 0 | 5G | 0 | 0 | 0 | 0 | 0 | 0 | 0 |

What is claimed is:

1. A compound of the formula:

$$JSO_2NHCNA \overset{W}{\underset{R}{\|}}$$

wherein
J is

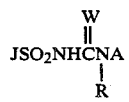

J-1

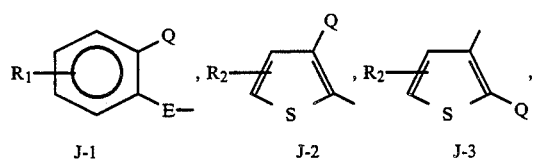

J-2, J-3

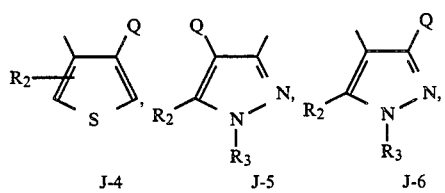

J-4, J-5, J-6

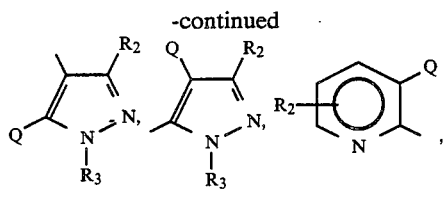

J-7, J-8, J-9

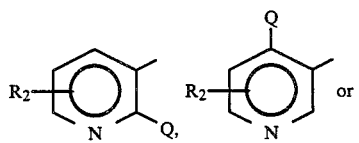

J-10, J-11

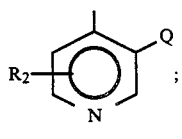

J-12

W is O or S;
R is H or CH$_3$;
E is a single bond or —CH$_2$—;
Q is Q$_2$ or Q$_3$;

$Q_2$ is

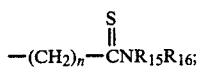

$Q_3$ is

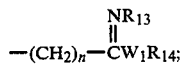

n is 0 or 1;
$W_1$ is O or S;
$R_1$ is H, $C_1$–$C_4$ alkyl, $C_1$–$C_3$ haloalkyl, Cl, Br, F, $NO_2$, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, CN, $CO_2R_c$, $C_1$–$C_3$ haloalkoxy, $C_1$–$C_3$ haloalkylthio, $CH_2OCH_3$, $CH_2SCH_3$, $CH_2CN$, $NH_2$, $NHCH_3$ or $N(CH_3)_2$;
$R_2$ is H, Cl, Br, $C_1$–$C_4$ alkyl, $C_1$–$C_3$ alkoxy or $C_1$–$C_3$ alkylthio;
$R_3$ is H, $C_1$–$C_4$ alkyl, $C_3$–$C_4$ alkenyl or phenyl;
$R_a$ is H, $C_1$–$C_4$ alkyl, $C_2$–$C_3$ cyanoalkyl or $C_1$–$C_3$ alkoxy;
$R_b$ is H, $C_1$–$C_4$ alkyl or $C_3$–$C_4$ alkenyl; or
$R_a$ and $R_b$ may be taken together as $(CH_2)_3$, $(CH_2)_4$, $(CH_2)_5$ or $CH_2CH_2OCH_2CH_2$;
$R_c$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;
$R_{13}$ is $C_1$–$C_4$ alkyl;
$R_{14}$ is $C_1$–$C_4$ alkyl;
$R_{15}$ is H, $C_1$–$C_6$ alkyl, $C_2$–$C_3$ alkyl substituted with $C_1$–$C_3$ alkoxy or phenoxy, $C_3$–$C_6$ alkenyl, $C_3$–$C_6$ alkynyl, $C_3$–$C_6$ cycloalkyl, $C_5$–$C_6$ cycloalkenyl, $C_4$–$C_7$ cycloalkylalkyl, $C_5$–$C_6$ cycloalkyl substituted with $CH_3$ or $OCH_3$, $CH_2CN$, $CH_2CH_2CN$, $OCH_3$, $OC_2H_5$, $N(CH_3)_2$,

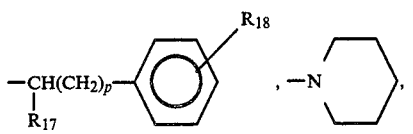

$R_{16}$ is H, $C_1$–$C_6$ alkyl, $CH_2CH=CH_2$, $CH_2CN$ or $CH_2CH_2CN$; or
$R_{15}$ and $R_{16}$ may be taken together to form $(CH_2)_3$, $(CH_2)_4$, $(CH_2)_5$, $(CH_2)_6$, $CH_2CH=CHCH_2$, $CH_2CH_2OCH_2CH_2$ or $CH_2CH_2N(CH_3)CH_2CH_2$;
$R_{17}$ is H or $CH_3$;
$R_{18}$ is H, $C_1$–$C_3$ alkyl, Cl, Br, $OCH_3$ or $OC_2H_5$;
$R_{19}$ is H, $C_1$–$C_4$ alkyl, $OCH_3$, F, Br, Cl, $CF_3$, CN, $NO_2$, $SO_2CH_3$, $SCH_3$ or $N(CH_3)_2$;
A is

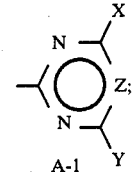

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkoxy, amino, $C_1$–$C_3$ alkylamino or di($C_1$–$C_3$)alkylamino;
Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$)alkylamino, $C_3$–$C_4$ alkenyloxy, $C_3$–$C_4$ alkynyloxy, $C_2$–$C_5$ alkylsulfinylalkyl, $C_1$–$C_4$ haloalkyl, $C_2$–$C_5$ alkylsulfonylalkyl, $C_3$–$C_5$ cycloalkyl, $C_2$–$C_4$ alkynyl, $C_2$–$C_5$ alkylthioalkyl,

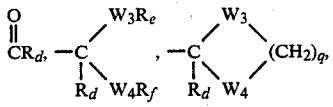

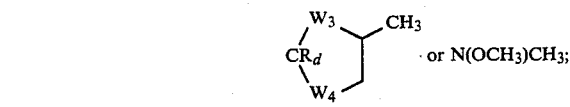

$W_3$ and $W_4$ are independently O or S;
q is 2 or 3;
$R_d$ is H or $CH_3$;
$R_e$ is $C_1$–$C_2$ alkyl;
$R_f$ is $C_1$–$C_2$ alkyl;
Z is CH;
and their agriculturally suitable salts;
provided that
(a) when W is S, then R is H and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

(b) when X is Cl, Br, F or I, then Y is $OCH_3$, $OC_2H_5$, $NH_2$, $NHCH_3$, $N(CH_3)_2$ or $OCF_2H$;
(c) the combined total number of carbon atoms of $R_{15}$ and $R_{16}$ is less than or equal to 10;
(d) when $R_{15}$ is $CH_2CN$ or $CH_2CH_2CN$, then $R_{16}$ is $CH_2CN$ or $CH_2CH_2CN$;
(e) when $R_{15}$ is $OCH_3$ or $OC_2H_5$, then $R_{16}$ is H or $CH_3$;
(f) when E is $-CH_2-$, then n is 0;
(g) when the total number of carbon atoms of X and Y is greater than four, then the number of carbons of $R_1$ is less than or equal to two, the number of carbons of $R_2$ is less than or equal to two, and the number of carbons of Q is less than or equal to four.

2. Compounds of claim 1 where
W is O;
R is H; and
$R_{14}$ is other than $C(CH_3)_3$.

3. Compounds of claim 2 where

X is CH$_3$, OCH$_3$, OC$_2$H$_5$, Cl, Br, F, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and Y is H, CH$_3$, OCH$_3$, OC$_2$H$_5$, CH$_2$OCH$_3$, NHCH$_3$, N(OCH$_3$)CH$_3$, N(CH$_3$)$_2$, C$_2$H$_5$, CF$_3$, SCH$_3$, OCH$_2$CH=CH$_2$, OCH$_2$C≡CH, CH$_2$OC$_2$H$_5$, OCH$_2$CH$_2$OCH$_3$, CH$_2$SCH$_3$, CH$_2$SC$_2$H$_5$, cyclopropyl,

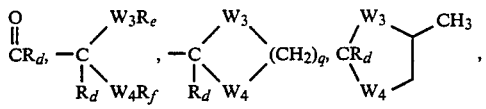

OCF$_2$H, SCF$_2$H, C≡CH or C≡CCH$_3$.

4. Compounds of claim 3 where

R$_{15}$ is H, C$_1$-C$_3$ alkyl, C$_3$-C$_4$ alkenyl or C$_3$-C$_4$ alkynyl;

R$_{16}$ is H, C$_1$-C$_3$ alkyl or CH$_2$CH=CH$_2$; or

R$_{15}$ and R$_{16}$ are taken together to form (CH$_2$)$_4$, (CH$_2$)$_5$ or CH$_2$CH$_2$OCH$_2$CH$_2$.

5. Compounds of claim 4 where

R$_2$ is H; and

R$_1$ is in the 5-position and selected from H, F, Cl, Br, C$_1$-C$_2$ alkyl, C$_1$-C$_3$ alkoxy or C$_1$-C$_3$ alkylthio.

6. Compounds of claim 5 where

X is CH$_3$, OCH$_3$, OC$_2$H$_5$, Cl, OCF$_2$H or OCH$_2$CF$_3$; and

Y is CH$_3$, OCH$_3$, C$_2$H$_5$, CH$_2$OCH$_3$, NHCH$_3$ or CH(OCH$_3$)$_2$.

7. Compounds of claim 6 where

R$_1$ is H, Cl, CH$_3$ or OCH$_3$;

n is 0; and

E is a single bond.

8. Compounds of claim 7 where

R$_{13}$ is C$_1$-C$_2$ alkyl;

R$_{14}$ is C$_1$-C$_2$ alkyl;

R$_{15}$ is H or C$_1$-C$_3$ alkyl; and

R$_{16}$ is H or C$_1$-C$_3$ alkyl.

9. Compounds of claim 8 where Q is —C(S)NR$_{15}$R$_{16}$.

10. Compounds of claim 8 where Q is —C(=NR$_{13}$)W$_1$R$_{14}$.

11. Compounds of claim 9 where J is J-1.
12. Compounds of claim 9 where J is J-2.
13. Compounds of claim 9 where J is J-3.
14. Compounds of claim 9 where J is J-4.
15. Compounds of claim 9 where J is J-5.
16. Compounds of claim 9 where J is J-6.
17. Compounds of claim 9 where J is J-7.
18. Compounds of claim 9 where J is J-8.
19. Compounds of claim 9 where J is J-9.
20. Compounds of claim 9 where J is J-10.
21. Compounds of claim 9 where J is J-11.
22. Compounds of claim 9 where J is J-12.
23. Compounds of claim 10 where J is J-1.
24. Compounds of claim 10 where J is J-2.
25. Compounds of claim 10 where J is J-3.
26. Compounds of claim 10 where J is J-4.
27. Compounds of claim 10 where J is J-5.
28. Compounds of claim 10 where J is J-6.
29. Compounds of claim 10 where J is J-7.
30. Compounds of claim 10 where J is J-8.
31. Compounds of claim 10 where J is J-9.
32. Compounds of claim 10 where J is J-10.
33. Compounds of claim 10 where J is J-11.
34. Compounds of claim 10 where J is J-12.

35. The compound of claim 1 which is N-[(4,6-dimethoxypyrimidin-2-yl)aminocarbonyl]-2-(1-pyrrolidinylthioxomethyl)benzenesulfonamide.

36. The compound of claim 1 which is 2-[[(4,6-dimethoxypyrimidin-2-yl)aminocarbonyl]aminosulfonyl]-N,N-dimethylbenzenecarbothioamide.

37. A composition suitable for controlling the growth of undesired vegetation which comprises an effective amount of the compound of claim 1 and at least one of the following: surfactant, solid or liquid diluent.

38. A composition suitable for controlling the growth of undesired vegetation which comprises an effective amount of the compound of claim 2 and at least one of the following: surfactant, solid or liquid diluent.

39. A composition suitable for controlling the growth of undesired vegetation which comprises an effective amount of the compound of claim 3 and at least one of the following: surfactant, solid or liquid diluent.

40. A composition suitable for controlling the growth of undesired vegetation which comprises an effective amount of the compound of claim 4 and at least one of the following: surfactant, solid or liquid diluent.

41. A composition suitable for controlling the growth of undesired vegetation which comprises an effective amount of the compound of claim 5 and at least one of the following: surfactant, solid or liquid diluent.

42. A composition suitable for controlling the growth of undesired vegetation which comprises an effective amount of the compound of claim 6 and at least one of the following: surfactant, solid or liquid diluent.

43. A composition suitable for controlling the growth of undesired vegetation which comprises an effective amount of the compound of claim 7 and at least one of the following: surfactant, solid or liquid diluent.

44. A composition suitable for controlling the growth of undesired vegetation which comprises an effective amount of the compound of claim 8 and at least one of the following: surfactant, solid or liquid diluent.

45. A composition suitable for controlling the growth of undesired vegetation which comprises an effective amount of the compound of claim 9 and at least one of the following: surfactant, solid or liquid diluent.

46. A composition suitable for controlling the growth of undesired vegetation which comprises an effective amount of the compound of claim 10 and at least one of the following surfactant, solid or liquid diluent.

47. A composition suitable for controlling the growth of undesired vegetation which comprises an effective amount of the compound of claim 11 and at least one of the following: surfactant, solid or liquid diluent.

48. A method for controlling the growth of undesired vegetation which comprises applying to the locus to be protected an effective amount of a compound of claim 1.

49. A method for controlling the growth of undesired vegetation which comprises applying to the locus to be protected an effective amount of a compound of claim 2.

50. A method for controlling the growth of undesired vegetation which comprises applying to the locus to be protected an effective amount of a compound of claim 3.

51. A method for controlling the growth of undesired vegetation which comprises applying to the locus to be protected an effective amount of a compound of claim 4.

52. A method for controlling the growth of undesired vegetation which comprises applying to the locus to be protected an effective amount of a compound of claim 5.

53. A method for controlling the growth of undesired vegetation which comprises applying to the locus to be protected an effective amount of a compound of claim 6.

54. A method for controlling the growth of undesired vegetation which comprises applying to the locus to be protected an effective amount of a compound of claim 7.

55. A method for controlling the growth of undesired vegetation which comprises applying to the locus to be protected an effective amount of a compound of claim 8.

56. A method for controlling the growth of undesired vegetation which comprises applying to the locus to be protected an effective amount of a compound of claim 9.

57. A method for controlling the growth of undesired vegetation which comprises applying to the locus to be protected an effective amount of a compound of claim 10.

58. A method for controlling the growth of undesired vegetation which comprises applying to the locus to be protected an effective amount of a compound of claim 11.

* * * * *

UNITED STATES PATENT AND TRADEMARK OFFICE
CERTIFICATE OF CORRECTION

PATENT NO. : 4,675,045
DATED : June 23, 1987
INVENTOR(S) : Wallace C. Petersen

It is certified that error appears in the above—identified patent and that said Letters Patent is hereby corrected as shown below:

In Claim 1, column 41, after line 66 and before "A is" in line 67, insert -- p is 0 or 1; --

Signed and Sealed this

Fifteenth Day of March, 1988

*Attest:*

DONALD J. QUIGG

*Attesting Officer*  *Commissioner of Patents and Trademarks*